(12) United States Patent
Guan et al.

(10) Patent No.: US 10,751,715 B1
(45) Date of Patent: Aug. 25, 2020

(54) MICROFLUIDIC REPORTER CELL ASSAY METHODS AND KITS THEREOF

(71) Applicant: Berkeley Lights, Inc., Emeryville, CA (US)

(72) Inventors: Xiao Guan, San Rafael, CA (US); Mark P. White, San Francisco, CA (US); Jason M. McEwen, El Cerrito, CA (US); Gang F. Wang, Mountain View, CA (US); Kevin T. Chapman, Santa Monica, CA (US); Xiaohua Wang, Albany, CA (US); Christine E. Sun, Emeryville, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 865 days.

(21) Appl. No.: 15/136,481

(22) Filed: Apr. 22, 2016

Related U.S. Application Data

(60) Provisional application No. 62/151,363, filed on Apr. 22, 2015.

(51) Int. Cl.
*B01L 3/00* (2006.01)
*C12M 1/02* (2006.01)
(Continued)

(52) U.S. Cl.
CPC ..... *B01L 3/50273* (2013.01); *B01L 3/502715* (2013.01); *C12M 23/16* (2013.01); *C12M 23/20* (2013.01); *C12M 23/34* (2013.01); *C12M 23/50* (2013.01); *C12M 23/58* (2013.01); *C12M 41/18* (2013.01); *C12M 41/32* (2013.01); *C12M 41/48* (2013.01); *C12Q 1/02* (2013.01); *G01N 33/5005* (2013.01); *B01L 2300/161* (2013.01);
(Continued)

(58) Field of Classification Search
CPC .......... B01L 3/50273; B01L 3/502715; C12M 23/50; C12M 41/18; C12M 41/32; C12M 23/34; C12M 23/16; C12Q 1/02; G01N 33/5005
See application file for complete search history.

(56) References Cited

U.S. PATENT DOCUMENTS 6,294,063 B1    9/2001   Becker
6,890,750 B1 *   5/2005   Zheng .................... C07H 21/02
                                                                       435/325

(Continued)

FOREIGN PATENT DOCUMENTS

KR    10-2010-0008222    1/2010
WO       2010147078      12/2010

OTHER PUBLICATIONS

Hung et al., Continuous Perfusion Microfluidic Cell Culture Array for High-Throughput Cell-Based Assays, Biotech and Bioengineering 89(1): 1-8 (2004).

(Continued)

*Primary Examiner* — Melanie Brown
(74) *Attorney, Agent, or Firm* — Kenneth E. Horton; Kirton McConkie

(57) ABSTRACT

Functional assays using reporter cell assays are described which probe the activity of at least one cell of interest. The ability to probe at least one cell is provided by using the microfluidic methods, devices and kits described herein. Assays combining both reporter cell signaling as well as binding assay signaling for at least one cell is also described herein.

23 Claims, 12 Drawing Sheets

(51) Int. Cl.

| | | |
|---|---|---|
| *C12M 1/34* | (2006.01) | |
| *C12M 1/36* | (2006.01) | |
| *C12M 1/00* | (2006.01) | |
| *C12M 3/06* | (2006.01) | |
| *C12Q 1/02* | (2006.01) | |
| *G01N 33/50* | (2006.01) | |

(52) U.S. Cl.
CPC . *B01L 2300/168* (2013.01); *B01L 2300/1822* (2013.01); *B01L 2400/0424* (2013.01); *B01L 2400/0454* (2013.01)

(56) References Cited

U.S. PATENT DOCUMENTS

| | | | |
|---|---|---|---|
| 7,090,759 B1 | 8/2006 | Seul | |
| 9,834,747 B2* | 12/2017 | Mershin | C12M 35/08 |
| 2002/0192717 A1* | 12/2002 | Kantor | G01N 33/554 |
| | | | 435/7.2 |
| 2003/0008364 A1 | 1/2003 | Wang | |
| 2003/0047456 A1 | 3/2003 | Medoro | |
| 2003/0215941 A1* | 11/2003 | Campbell | B82Y 30/00 |
| | | | 435/325 |
| 2004/0072278 A1 | 4/2004 | Chou | |
| 2004/0115838 A1* | 6/2004 | Quake | B01D 57/02 |
| | | | 436/538 |
| 2004/0191789 A1 | 9/2004 | Manaresi | |
| 2004/0197905 A1 | 10/2004 | Hafeman | |
| 2005/0112548 A1 | 5/2005 | Segawa | |
| 2005/0129581 A1 | 6/2005 | McBride | |
| 2005/0175981 A1 | 8/2005 | Voldman | |
| 2006/0091015 A1 | 5/2006 | Lau | |
| 2006/0154361 A1 | 7/2006 | Wikswo | |
| 2007/0072187 A1* | 3/2007 | Blok | B01L 3/5085 |
| | | | 435/6.14 |
| 2007/0095669 A1 | 5/2007 | Lau | |
| 2007/0183934 A1 | 8/2007 | Diercks | |
| 2008/0102478 A1* | 5/2008 | Li | B01L 3/5027 |
| | | | 435/7.23 |
| 2008/0302732 A1 | 12/2008 | Soh | |
| 2009/0023608 A1 | 1/2009 | Hung | |
| 2009/0170186 A1 | 7/2009 | Wu | |
| 2010/0003666 A1 | 1/2010 | Lee | |
| 2010/0101960 A1 | 4/2010 | Ohta | |
| 2010/0273681 A1 | 10/2010 | Cerrina | |
| 2011/0053151 A1 | 3/2011 | Hansen et al. | |
| 2011/0117634 A1 | 5/2011 | Halamish | |
| 2011/0143964 A1 | 6/2011 | Zhou | |
| 2011/0262906 A1 | 10/2011 | Dimov | |
| 2012/0009671 A1 | 1/2012 | Hansen et al. | |
| 2012/0015347 A1 | 1/2012 | Singhal et al. | |
| 2012/0118740 A1 | 5/2012 | Garcia | |
| 2012/0148140 A1 | 6/2012 | Di Carlo | |
| 2012/0156675 A1 | 6/2012 | Lueerssen | |
| 2012/0325665 A1 | 12/2012 | Chiou | |
| 2013/0115606 A1* | 5/2013 | Hansen | C12M 29/10 |
| | | | 435/6.12 |
| 2013/0118905 A1 | 5/2013 | Morimoto | |
| 2013/0171628 A1 | 7/2013 | DiCarlo | |
| 2013/0190212 A1 | 7/2013 | Handique | |
| 2013/0204076 A1 | 8/2013 | Han | |
| 2013/0261021 A1 | 10/2013 | Bocchi | |
| 2014/0116881 A1 | 5/2014 | Chapman | |
| 2014/0120558 A1 | 5/2014 | Chapman | |
| 2015/0018226 A1 | 1/2015 | Hansen | |
| 2015/0151298 A1 | 4/2015 | Hobbs | |
| 2015/0151307 A1 | 4/2015 | Breinlinger | |
| 2015/0165436 A1 | 6/2015 | Chapman | |
| 2016/0025761 A1* | 1/2016 | West | G01N 15/1056 |
| | | | 506/7 |
| 2016/0171686 A1 | 6/2016 | Du | |
| 2016/0184821 A1 | 6/2016 | Hobbs | |
| 2016/0193604 A1 | 7/2016 | McFarland | |
| 2016/0252495 A1 | 9/2016 | Ricicova | |
| 2016/0312165 A1 | 10/2016 | Lowe | |

OTHER PUBLICATIONS

Chiou et al., "Massively Parallel Manipulation of Single Cells and Microparticles Using Optical Images", Nature, vol. 436, pp. 370-372, 2005.

Chiou, Pei-Yu, "Massively Parallel Optical Manipulation of Cells, Micro- and Nano-Particles on Optoelectronic Devices", Dissertation, University of California at Berkeley, 2005 (147 pages).

Yi et al., "Microfluidics Technology for Manipulation and Analysis of Biological Cells", Analytica Chimica Acta, vol. 560, pp. 01-23, 2006.

Iliescu et al., "Continuous Field-Flow Separation of Particle Populations in a Dielectrophoretic Chip with Three Dimensional Electrodes", Applied Physics Letters, vol. 90, Issue 23, 234104, 2007.

Nevill et al., "Integrated microfluidic cell culture and lysis on a chip", vol. 07, No. 12, pp. 1689-1695, 2007.

Valley et al., "Optoelectronic Tweezers as a Tool for Parallel Single-Cell Manipulation and Stimulation", IEEE Transactions on Biomedical Circuits and Systems, vol. 3, No. 6, pp. 424-431, 2009.

Hsu et al., Sorting of Differentiated Neurons using Phototransistor-based Optoelectronic Tweezers for Cell Replacement Therapy of Neurodegenerative Diseases, IEEE Conference on Transducers (Jun. 21-25, 2009).

Xu, Guolin et al,. Recent Trends in Dielectrophoresis, Informacije MIDEM, 2010, vol. 40, Issue No. 4, pp. 253-262.

Young et al., "Fundamentals of microfluidic cell culture in controlled microenvironments", Chem Soc Rev, vol. 39, No. 3, pp. 1036-1048, 2010.

Chung et al., "Imaging single-cell signaling dynamics with a deterministic high-density single-cell trap array", Anal. Chem., vol. 83, No. 18, pp. 7044-7052, 2011.

Somaweera et al., "Generation of a Chemical Gradient Across an Array of 256 Cell Cultures in a Single Chip", Analyst., vol. 138, No. 19, pp. 5566-5571, 2013.

\* cited by examiner

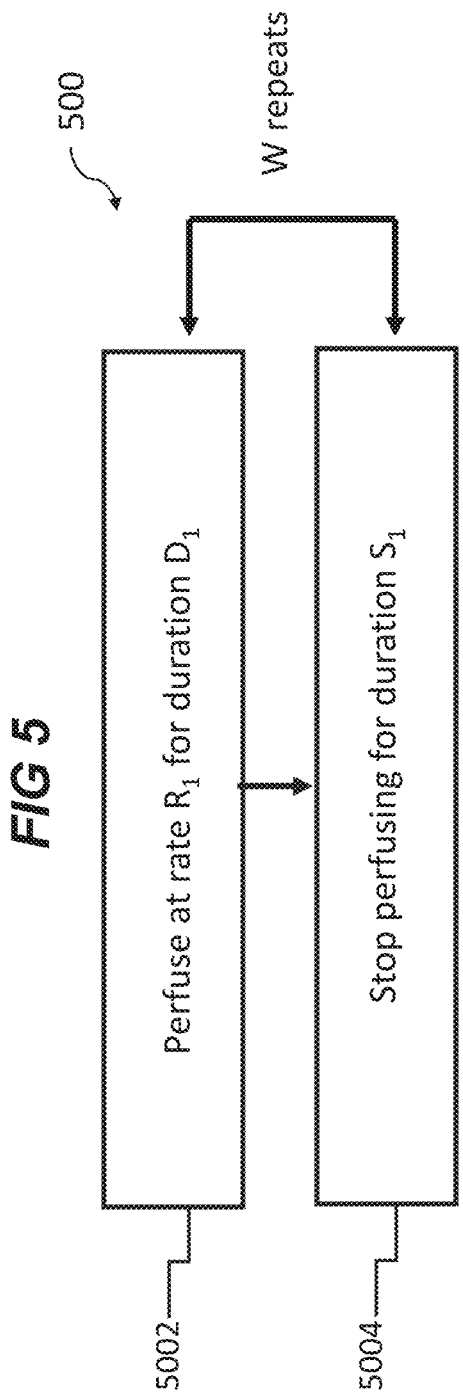

US 10,751,715 B1

MICROFLUIDIC REPORTER CELL ASSAY METHODS AND KITS THEREOF

This application is a non-provisional application claiming the benefit under 35 U.S.C. 119(e) of U.S. Provisional Application No. 62/151,363 filed on Apr. 22, 2015, which disclosure is herein incorporated by reference in its entirety.

CROSS REFERENCE

This application cross-references U.S. application Ser. No. 15/135,707, entitled "Microfluidic Cell Culture", filed on Apr. 22, 2016, which disclosure is herein incorporated by reference in its entirety.

BACKGROUND

Reporter cell assays are useful probes of the biological function of a cell, yielding information on the status of the cell. This type of information is not easily obtainable from other classes of assays, such as binding assays or cell surface stains. While reporter cell assays have been performed within reaction well format or flow cytometry format, investigation of the status of at least one cell, is not readily performed. There is need for improvement in this field in order to support basic biological research, pharmaceutical research and development, medical diagnostics and treatment as well as for bioproduction of cells expressing useful biological/chemical species.

SUMMARY

In a first aspect, a system is provided for assaying at least one biological cell of interest in a microfluidic device, including a microfluidic device comprising a flow region configured to contain a flow of a first fluidic medium and at least one incubation chamber, and wherein the incubation chamber is configured to contain at least one reporter cell and the at least one biological cell of interest; and at least one reporter cell. The at least one incubation chamber may include an isolation region and a connection region, wherein the isolation region is fluidically connected to the connection region and the connection region comprises an opening directly into the flow region.

In various embodiments of the system, the at least one incubation chamber may be configured to contain no more than a single biological cell of interest. In some embodiments, the at least one incubation chamber may be configured to contain a plurality of biological cells of interest. The at least one incubation chamber may be configured to isolate the at least one reporter cell and the at least one biological cell of interest. the incubation chamber is configured to locate the at least one reporter cell and the at least one biological cell of interest at spatially distinct locations within the incubation chamber. In some embodiments, the microfluidic device may further include a flow channel including at least a portion of the flow region, and wherein the at least one incubation chamber includes a connection region that opens directly into the flow channel. In some embodiments, the isolation region of the at least one incubation chamber may be fluidically connected to the flow channel via the connection region and is configured to contain a second fluidic medium, where when the flow region and the at least one incubation chamber are substantially filled with the first and second fluidic media respectively, then components of the second fluidic medium diffuse into the first fluidic medium and/or components of the first fluidic medium diffuse into the second fluidic medium; and the first medium does not substantially flow into the isolation region.

In various embodiments of the system, the at least one reporter cell may be configured to provide a detectable signal. In some embodiments, the detectable signal may be produced when the at least one biological cell of interest includes a biological activity of interest. In other embodiments, the at least one reporter cell may be configured to produce a different detectable signal when the at least one biological cells of interest does not comprise the biological activity of interest. The detectable signal of the at least one reporter cell may be colorimetric, fluorescent, or bioluminescent.

In various embodiments of the system, the flow region of the microfluidic device may further include one or more capture micro-objects. In various embodiments, each of the one or more capture micro-objects may include a binding substance configured to specifically bind to a biological product of the at least one biological cell of interest. In some embodiments, the biological product may be a secreted biological product. In various embodiments, the biological product may be bound to the binding substance of the one or more capture micro-object thereby producing a bound capture micro-object. In some embodiments, each of the one or more capture micro-objects may be a bound capture micro-object. The one or more bound capture micro-objects may be configured to be detectable. The one or more bound capture micro-objects may be indirectly or directly detectable. The detectable signal of the one or more bound capture micro-objects may be colorimetric, fluorescent, or chemiluminescent. In some embodiments, the one or more capture micro-objects may include a bead. In some embodiments, the one or more capture micro-objects may include a magnetic bead.

In various embodiments of the system, the one or more capture micro-objects may be in fluid connection with the one or more biological cells of interest. In some embodiments, the one or more capture micro-objects may be located in the connection region of the incubation chamber or in the flow region proximal to the incubation chamber. In other embodiments, the one or more capture micro-objects may be located at a location within the microfluidic device other than in the isolation region of the incubation chamber.

In various embodiments of the system, the detectable signal of the at least one reporter cells and the detectable signal of the one or more bound capture micro-objects may be spectrally distinct.

In various embodiments of the system, the microfluidic device may further include at least one inlet port configured to input the first or second fluidic medium into the flow region and at least one outlet port may be configured to receive the first medium as it exits from the flow region. In various embodiments, the microfluidic device may be configured to perfuse the first medium to maintain cell viability. In some embodiments, the microfluidic device may be configured to perfuse the first medium irregularly. In other embodiments, the microfluidic device may be configured to perfuse the first medium periodically.

In various embodiments of the system, the microfluidic device may include a substrate configured to generate a dielectrophoresis (DEP) force, wherein a surface of the substrate may form a surface of the incubation chamber and the flow region. In various embodiments, the dielectrophoretic substrate is optically actuated. In some embodiments, the substrate may include a plurality of electrodes wherein the plurality of electrodes is configured to generate a dielectrophoresis (DEP) force. In some embodiments, the system may further include a selector control module configured to activate and deactivate each of the plurality of electrodes, wherein activation of an electrode generates a dielectrophoresis (DEP) force sufficiently strong to move the at least one biological cell into or out of the at least one incubation chamber or the isolation region thereof. In some embodiments, each of the plurality of electrodes may be optically actuated. In other embodiments, the microfluidic device may further include a substrate having an electrode connected to a plurality of transistors, wherein a surface of the substrate may form a surface of the incubation chamber and the flow region. In some embodiments, each transistor of the plurality may be configured to generate a dielectrophoresis (DEP) force. In some embodiments, the system may further include a selector control module configured to activate and deactivate each of the plurality of transistors, thereby generating a dielectrophoresis (DEP) force sufficiently strong to move at least one biological cell into or out of the at least one incubation chamber or the isolation region thereof. In some embodiments, each of the plurality of transistors may be optically actuated. In various other embodiments, the microfluidic device may further include a substrate having an electrode and a layer of amorphous silicon, wherein a surface of the substrate may form a surface of the incubation chamber and the flow region. In some embodiments, the system may further include a selector control module configured to activate and deactivate the virtual electrode in the layer of amorphous silicon, thereby generating a dielectrophoresis (DEP) force sufficiently strong to move at least one biological cell into or out of the at least one incubation chamber or the isolation region thereof. In some embodiments, the layer of amorphous silicon may be optically activated. In various embodiments, the DEP force may be produced by optoelectronic tweezers (OET).

In various embodiments of the system, the at least one reporter cell is moved into or out of the at least one incubation chamber or the isolation region thereof by fluid flow and/or gravity.

In various embodiments of the system, the at least one incubation chamber of the microfluidic device may have at least one surface conditioned to support cell growth, viability, portability, or any combination thereof. In some embodiments, the at least one conditioned surface of the incubation chamber may include a polymer. In some embodiments, the polymer of the at least one conditioned surface of the microfluidic device may include alkylene oxide moieties, amino acid moieties or saccharide moieties. In various embodiments, the at least one conditioned surface of the microfluidic device may include a covalently linked conditioned surface. In various embodiments, the covalently linked conditioned surface may include alkylene ether moieties, alkyl moieties, fluoroalkyl moieties, amino acid moieties, or saccharide moieties. In some embodiments, the covalently linked conditioned surface may be linked to the surface via a siloxy linking group. In various embodiments, the conditioned surface may be a monolayer.

In various embodiments of the system, the microfluidic device may include a plurality of incubation chambers. In various embodiments, no more than one biological cell may be introduced into each of the plurality of incubation chambers. In various embodiments, the at least one biological cell may include a mammalian cell. In some embodiments, the at least one biological cell may include a hybridoma cell. In other embodiments, the at least one biological cell may include a lymphocyte or a leukocyte. In various embodiments, the at least one biological cell may include a B cell, T cell, NK cell, dendritic cell, or macrophage. In various embodiments, the at least one biological cell may include an adherent cell.

In various embodiments of the system, the system may further include a light source configured to provide excitation energy to a moiety configured to be detectable by fluorescence. In various embodiments of the system, the system may further include a detector configured to capture an image of the at least one incubation chamber and any biological cells contained therein. In various embodiments, the detector may capture images under visible, infrared, or ultraviolet wavelengths of light.

In another aspect, a method is provided for assaying at least one biological cell for a biological activity in a system comprising a microfluidic device having at least one incubation chamber and a flow region, the method including the steps of introducing the at least one biological cell into the at least one incubation chamber; introducing one or more reporter cells into the at least one incubation chamber; and analyzing the one or more reporter cells for an activity stimulated by the presence of a biological activity of the at least one biological cell. The at least one incubation chamber may include an isolation region and a connection region, wherein the isolation region may be fluidically connected to the connection region and the connection region may include an opening directly into the flow region.

In various embodiments of the method, the one or more reporter cells may be configured to produce a detectable signal when the at least one biological cell comprises the biological activity. In some embodiments, the detectable signal of the one or more reporter cells may be a colorometric, fluorescent, or bioluminescent signal.

In various embodiments of the method, the step of introducing the one or more reporter cells may be performed before the step of introducing the at least one biological cell. In various embodiments of the method, the step of introducing the one or more reporter cells may be performed after the step of introducing the at least one biological cell.

In various embodiments of the method, the method may further include a step of introducing the one or more reporter cells to an isolation region of the at least one incubation chamber. In various other embodiments of the method, the method may further include a step of introducing the at least one biological cell into an isolation region of the at least one incubation chamber. In some embodiments, a single biological cell may be introduced into the isolation region of the incubation chamber. In various embodiments of the method, the method may further include a step of introducing the at least one biological cell to a spatially distinct region of the isolation region from the location of the one or more reporter cells.

In various embodiments of the method, the step of analyzing may include incubating the at least one biological cell and the one or more reporter cells in the at least one incubation chamber for a pre-determined period of time, thereby producing the detectable signal of the one or more reporter cells. In various embodiments of the method, the step of incubating may further include providing the one or more reporter cells with one or more reagents forming one or all of the components of the detectable signal of the one or more reporter cells. In various embodiments of the method, the step of analyzing may further include analyzing the one or more reporter cells at more than one time point during the incubation period. In various embodiments of the method, the step of analyzing the one or more reporter cells may further include providing excitation light to excite a fluorophore of the detectable signal of the one or more reporter cells.

In various embodiments of the method, the method may further include a step of detecting the detectable signal of the one or more reporter cells. In various embodiments of the method, the method may further include a step of quantifying the detectable signal of the one or more reporter cells, thereby quantifying the presence of the biological activity.

In various embodiments of the method, the one or more reporter cells may be configured to produce a second detectable signal when the at least one biological cell does not comprise the biological activity.

In various embodiments of the method, the step of incubating the at least one biological cell and the one or more reporter cells for the pre-determined period of time may include producing the second detectable signal of the one or more reporter cells, thereby indicating an absence of the biological activity. In various embodiments of the method, the step of analyzing the one or more reporter cells may further include providing excitation light to excite a fluorophore of the second detectable signal of the one or more reporter cells. In various embodiments of the method, the method may further include a step of detecting the second detectable signal of the one or more reporter cells. In various embodiments of the method, the method may further include a step of quantifying the detectable signal of the one or more reporter cells, thereby quantifying the absence of the biological activity.

In various embodiments of the method, the method may further include a step of introducing at least one capture micro-object into at least the flow region. In some embodiments, the step of introducing the at least one micro-object may further include disposing the at least one micro-object in a location adjacent to a proximal opening of the incubation chamber in the flow region. In some embodiments, introducing the at least one capture micro-object may not include introducing the at least one capture micro-object to the isolation region of the incubation chamber.

In various embodiments of the method, each of the one or more capture micro-objects may include a binding substance configured to specifically bind a biological product of the at least one biological cells, thereby forming a bound capture micro-object configured to be detectable. In some embodiments, the binding substance may be covalently attached to each of the one or more micro-objects. In other embodiments, the binding substance may be noncovalently attached to each of the one or more micro-objects. In some embodiments, the bound capture micro-object is configured to be directly detectable. In some embodiments, the bound capture micro-object is configured to be indirectly detectable. A detectable signal of the bound capture micro-object may be a colorimetric, fluorescent, or chemiluminescent signal. In some embodiments, the at least one capture micro-object may be a bead. In various embodiments, the biological product of the at least one biological cell may be a secreted biological product.

In various embodiments of the method, the method may further include a step of incubating the at least one capture micro-object during the incubation period, thereby producing the at least one bound capture micro-object. In various embodiments of the method, the method may further include a step of introducing one or more visualization reagents which may be configured to bind to the bound capture micro-object to produce the detectable signal. In various embodiments of the method, the method may further include a step of providing excitation light to excite the detectable signal of the bound capture micro-object. In various embodiments of the method, the method may further include a step of detecting the detectable signal of the bound capture micro-object. In various embodiments of the method, the method may further include a step of quantifying the detected signal of the binding substance. In various embodiments of the method, the method may further include a step of introducing the at least one capture micro-object using a magnetic field. In various embodiments of the method, the system may be any system as described herein.

In various embodiments of the method, the step of introducing the at least one biological cell into the microfluidic device, incubation chamber, isolation region or location within the isolation region thereof, may include using a dielectrophoresis (DEP) force having sufficient strength to move the biological cell. In some embodiments, the step of using the DEP force includes optically actuating the DEP force. In some embodiments, the step of introducing the one or more reporter cells into the at least one incubation chamber may include using fluid flow and/or gravity. In some embodiments, the step of introducing the one or more capture micro-objects into the flow region may include using fluid flow and/or gravity.

In some embodiments of the method, the method may further include a step of introducing a first fluidic medium into a flow channel of the flow region of the microfluidic device. The rate of introducing the first fluidic medium may not sweep the isolation region of the incubation chamber. In some embodiments of the method, the method may further include a step of perfusing the first fluidic medium during the incubating step, wherein the first fluidic medium is introduced via at least one inlet port of the microfluidic device and is exported via at least one outlet of the microfluidic device and further wherein the first fluidic medium may optionally include components from the second fluidic medium. In some embodiments, the perfusing may be non-continuous. In other embodiments, the perfusing may be periodic. In some embodiments of the method, the method may further include a step of perfusing the first fluidic medium at a rate sufficient to permit components of the second fluidic medium in the isolation region to diffuse into the first fluidic medium in the flow region and/or components of the first fluidic medium to diffuse into the second fluidic medium in the isolation region; and at the rate wherein the first medium does not substantially flow into the isolation region.

In some embodiments of the method, the at least one biological cell may include a mammalian cell. In other embodiments of the method, the at least one biological cell may include a hybridoma cell. In yet other embodiments of the method, the at least one biological cell may include a lymphocyte or a leukocyte. In some other embodiments of the method, the at least one biological cell may include a B cell, T cell, NK cell, dendritic cell, or macrophage. In further embodiments of the method, the at least one biological cell may include an adherent cell.

In some embodiments of the method, the method may further include a step of replenishing the conditioned surface.

In another aspect, a composition is provided including a biological cell and one or more reporter cells in an isolation region of a microfluidic device, where the one or more reporter cells are configured to detect a biological activity of the biological cell when contacted by a first extracellular species produced by the biological cell. In some embodiments, the biological cell and one or more reporter cells cell may be at least one biological cell and one or more reporter cells. The microfluidic device of the compositions may have at least one incubation chamber and a flow region, where the at least one incubation chamber includes an isolation region and a connection region, wherein the isolation region is fluidically connected to the connection region and the connection region comprises an opening directly into the flow region. The microfluidic device may include at least one conditioned surface configured to support cell growth, viability, portability or any combination thereof.

The at least one conditioned surface may include an alkylene ether moiety configured to support cell growth, viability, portability or any combination thereof. In other embodiments, the at least one conditioned surface may include an alkyl or fluoroalkyl (including perfluoroalkyl) moiety configured to support cell growth, viability, portability or any combination thereof. In some other embodiments, the at least one conditioned surface may include a dextran moiety configured to support cell growth, viability, portability or any combination thereof. In some embodiments, the biological cell and one or more reporter cells may be in contact with the at least one conditioned surface.

In some embodiments, a first extracellular species may be produced by the biological cell contacts the one or more reporter cells without the biological cell directly contacting any of the one or more reporter cells. In some embodiments, when the one or more reporter cells are contacted by the first extracellular species, then the one or more reporter cells may be configured to produce a first detectable signal. In some embodiments, the first detectable signal of the one or more reporter cells may include a colorimetric, fluorescent, bioluminescent or luminescent signal.

In various embodiments, the composition may further include at least one capture micro-object, wherein the at least one capture micro-object may be configured to bind an extracellular species produced by the biological cell, without physically contacting the biological cell.

In some embodiments, the extracellular species produced by the biological cell that binds to the at least one capture micro-object may be different from the extracellular species produced by the single biological cell that is detected by the one or more reporter cells. In various embodiments, the at least one capture micro-object may not be located within the isolation region.

In various embodiments of the composition, the at least one capture micro-object may be configured to form at least one detectable bound capture micro-object when the extracellular species binds to the at least one capture micro-object. In some embodiments, the at least one bound capture micro-object may be directly detectable. In other embodiments, the at least one bound capture micro-object may be indirectly detectable. In various embodiments, a detectable signal of the at least one bound capture micro-object may be fluorescent or chemiluminescent.

In some embodiments of the composition, the biological cell may include a mammalian cell. In other embodiments of the composition, the biological cell may include a hybridoma cell. In some embodiments of the composition, the biological cell may include a lymphocyte or a leukocyte. In further embodiments, the biological cell may include a B cell, T cell, NK cell, or macrophage. In some other embodiments, the biological cell may include an adherent cell.

In another aspect, a kit is provided, including a microfluidic device comprising at least one incubation chamber and a flow region; and one or more reporter cells configured to test for a biological activity of a biological cell. In some embodiments, the at least one incubation chamber of the microfluidic device may include an isolation region and a connection region, wherein the isolation region may be fluidically connected to the connection region and the connection region may include an opening directly into the flow region. In some embodiments, the microfluidic device may further include a flow channel comprising at least a portion of the flow region, and the incubation chamber may include a connection region that opens directly into the flow channel. In some embodiments, the at least one incubation chamber may further include an isolation region. In some embodiments, the isolation region may be fluidically connected to the connection region and may be configured to contain a second fluidic medium, wherein: when the flow region and the at least one incubation chamber are substantially filled with the first and second fluidic media respectively, then components of the second fluidic medium may diffuse into the first fluidic medium and/or components of the first fluidic medium may diffuse into the second fluidic medium; and the first medium may not substantially flow into the isolation region. In some embodiments, the at least one incubation chamber may be a plurality of isolation chambers. In various embodiments, the microfluidic device may further include at least one inlet port configured to input the first or second fluidic medium into the flow region and at least one outlet configured to receive the first medium as it exits from the flow region, wherein the first medium may optionally contain components of the second fluidic medium.

In various embodiments of the kit, the microfluidic device may further include a substrate having a dielectrophoresis (DEP) configuration wherein a surface of the substrate may form a surface of the incubation chamber and the flow region. The DEP configuration may be optically actuated.

In some embodiments of the kit, the kit may further include one or more micro-objects configured to bind a biological product of a biological cell.

In some embodiments of the kit, the kit may further include one or more reagents used to provide a detectable signal from the reporter cells configured to test for a biological activity of the biological cell.

In some embodiments of the kit, the microfluidic device may further include at least one conditioned surface configured to support cell growth, viability, portability or any combination thereof. In some embodiments of the kit, the kit may further include a reagent to replenish the conditioned surface. In some embodiments, the at least one conditioned surface of the at least one incubation chamber may include a polymer. In various embodiments, the polymer of the at least one conditioned surface of the microfluidic device may include alkylene oxide moieties, amino acid moieties or saccharide moieties. In other embodiments, the at least one conditioned surface of the microfluidic device may include a covalently linked conditioned surface. In various embodiments, the covalently linked conditioned surface may include alkylene ether moieties, alkyl moieties, fluoroalkyl moieties, amino acid moieties, or saccharide moieties. In some embodiments, the covalently linked conditioned surface may be linked to the surface via a siloxy linking group.

DETAILED DESCRIPTION

Reporter cell assays may be performed within a microfluidic device as described herein, where the behavior of at least one cell is examined. The ability to assay at least one biological cell of interest within an isolation region and obtain both location dependent and time dependent reporter signals provides more precise and selective data. While the microfluidic environment provides the ability to isolate one or more biological cells for investigation, it also offers the opportunity to multiplex assays to probe sets of individual cells of interest. The instant methods also offer the opportunity to simultaneously employ capture agents having specific binding partners in order to multiplex a reporter cell assay with one or more binding assays. Particularly with the motive forces available within the system used with the instant microfluidic devices, improved methods are provided for probing and linking assay data with specific cells of interest within a population of cells introduced into the microfluidic device.

BRIEF DESCRIPTION OF THE DRAWINGS

FIG. 5 is an example of one embodiment of a process for perfusing a fluidic medium in a microfluidic device.

Figure 1:
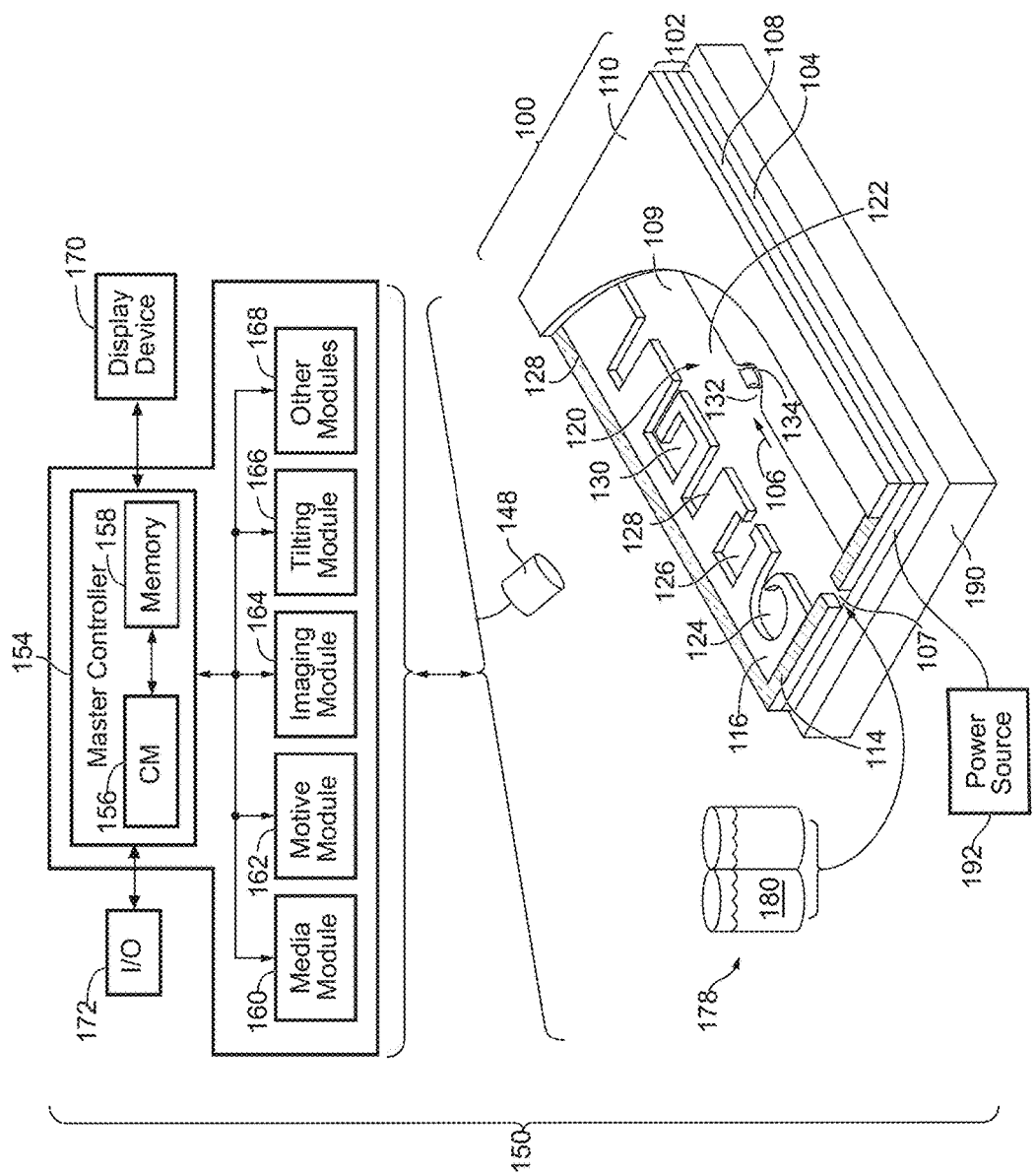
FIG. 1 illustrates an example of a system for use with a microfluidic device and associated control equipment according to some embodiments of the invention.

As used herein, "substantially" means sufficient to work for the intended purpose. As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments as a filtered, controlled composition and may be conditioned as described herein.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements are configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 300 times the length, at least 400 times the length, at least 500 times the length, or longer. In some embodiments, the length of a flow channel is in the range of from about 20,000 microns to about 100,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic incubation chamber and a microfluidic channel, or a connection region and an isolation region of a microfluidic incubation chamber.

As used herein, the term "constriction" refers generally to a narrowing of a width of a circuit element (or an interface between two circuit elements) in a microfluidic device. The constriction can be located, for example, at the interface between a microfluidic incubation chamber and a microfluidic channel, or at the interface between an isolation region and a connection region of a microfluidic incubation chamber.

As used herein, the term "transparent" refers to a material which allows visible light to pass through without substantially altering the light as is passes through.

As used herein, the term "micro-object" can encompass one or more of the following: inanimate micro-objects such as microparticles, microbeads (e.g., polystyrene beads, Luminex™ beads, or the like), magnetic beads, paramagnetic beads, microrods, microwires, quantum dots, and the like; biological micro-objects such as cells (e.g., embryos, oocytes, sperms, cells dissociated from a tissue, blood cells, immunological cells, including T cells, B cells, macrophages, NK cells, dendritic cells (DCs), and the like, hybridomas, cultured cells, cells dissociated from a tissue, cells from a cell line, such as CHO cells, which may be transfected and/or transformed, cancer cells, including circulating tumor cells (CTCs), infected cells, reporter cells, and the like), liposomes (e.g., synthetic or derived from membrane preparations), lipid nanorafts, and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "cell" refers to a biological cell, which can be a plant cell, an animal cell (e.g., a mammalian cell), a bacterial cell, a fungal cell, or the like. A mammalian cell can be, for example, from a human, a mouse, a rat, a horse, a goat, a sheep, a cow, a primate, or the like.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "non-sweeping" rate of fluidic medium flow means a rate of flow sufficient to permit components of a second fluidic medium in an isolation region of the incubation chamber to diffuse into the first fluidic medium in the flow region and/or components of the first fluidic medium to diffuse into the second fluidic medium in the isolation region; and further wherein the first medium does not substantially flow into the isolation region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials can be assayed in such a microfluidic device. For example, sample material comprising biological micro-objects to be assayed for production of an analyte of interest can be loaded into a swept region of the microfluidic device. Ones of the biological micro-objects can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1 illustrates an example of a microfluidic device 100 and a system 150 which can be used in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic incubation chambers 124, 126, 128, and 130, each having one or more openings in fluidic communication with flow path 106. As discussed further below, the microfluidic incubation chambers comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over incubation chambers 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 can further comprise a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 00 relative to x- and y-axes), a vertical orientation (i.e. at 900 relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.10, 0.20, 0.30, 0.4°, 0.5°, 0.6°, 0.7°, 0.8°, 0.9°, 1°, 2°, 30, 4°, 5°, 10°, 15°, 20°, 25°, 30°, 35, 40°, 45, 50°, 55° 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more incubation chambers. The term "above" as used herein denotes that the flow path 106 is positioned higher than the one or more incubation chambers on a vertical axis defined by the force of gravity (i.e. an object in an incubation chamber above a flow path 106 would have a higher gravitational potential energy than an object in the flow path). The term "below" as used herein denotes that the flow path 106 is positioned lower than the one or more incubation chambers on a vertical axis defined by the force of gravity (i.e. an object in an incubation chamber below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more incubation chambers without being located directly above or below the incubation chambers. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or incubation chambers 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more incubation chambers via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and incubation chambers 124, 126, 128, 130. Each chamber comprises an opening to channel 122, but otherwise is enclosed such that the chambers can substantially isolate micro-objects inside the chamber from fluidic medium 180 and/or micro-objects in the flow path 106 of channel 122 or in other chambers. In some instances, chambers 124, 126, 128, 130 are configured to physically corral one or more micro-objects within the microfluidic circuit 120. Incubation chambers in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic incubation chambers. Although five incubation chambers are shown, microfluidic circuit 120 may have fewer or more incubation chambers. In some embodiments, the microfluidic circuit 120 comprises a plurality of microfluidic incubation chambers, wherein two or more of the incubation chambers comprise differing structures and/or features.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of incubation chambers is configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic incubation chambers 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic incubation chamber, such that upon tilting the microfluidic device 100 about an axis parallel to the channel 122, the trapped micro-object exits the trap 132 at a trajectory that causes the micro-object to fall into the opening of the incubation chamber. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the incubation chambers) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic incubation chamber. In some embodiments, DEP forces are used to prevent a micro-object within an incubation chamber (e.g., incubation chamber 124, 126, 128, or 130) from being displaced therefrom. Further, in some embodiments, DEP forces are used to selectively remove a micro-object from an incubation chamber that was previously collected in accordance with the teachings of the instant invention. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the incubation chambers) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic incubation chamber. In some embodiments, OEW forces are used to prevent a droplet within an incubation chamber (e.g., incubation chamber 124, 126, 128, or 130) from being displaced therefrom. Further, in some embodiments, OEW forces are used to selectively remove a droplet from an incubation chamber that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic incubation chambers, and the force of gravity can transport the micro-objects and/or droplets into the chambers. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
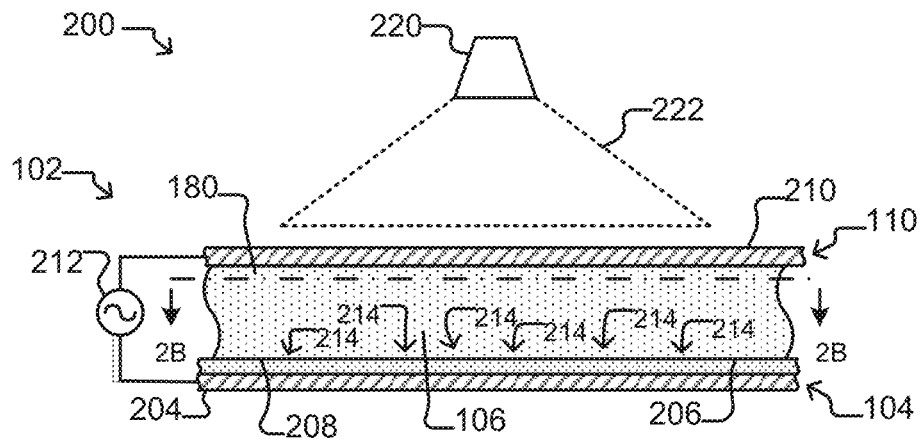
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive microfluidic device configurations. As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
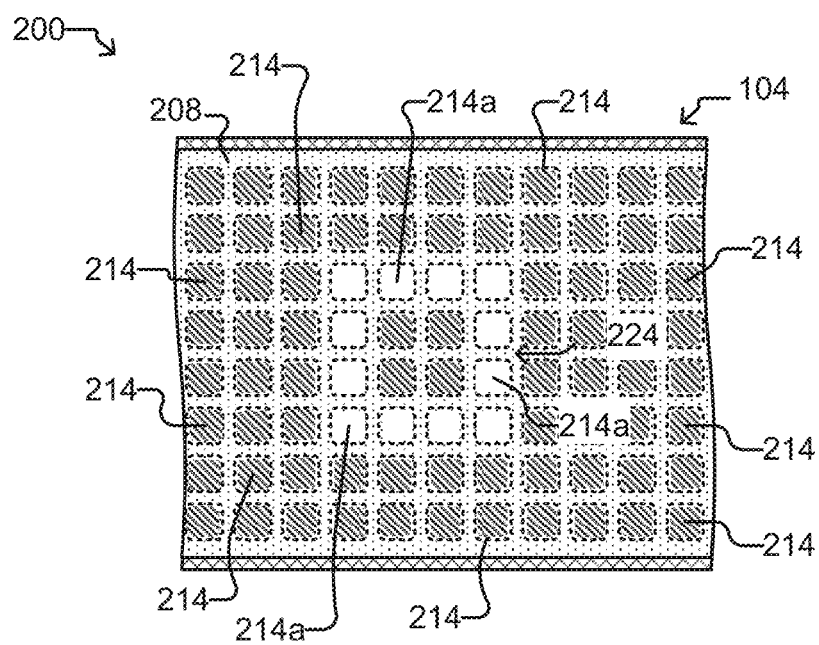
Figure 2C:
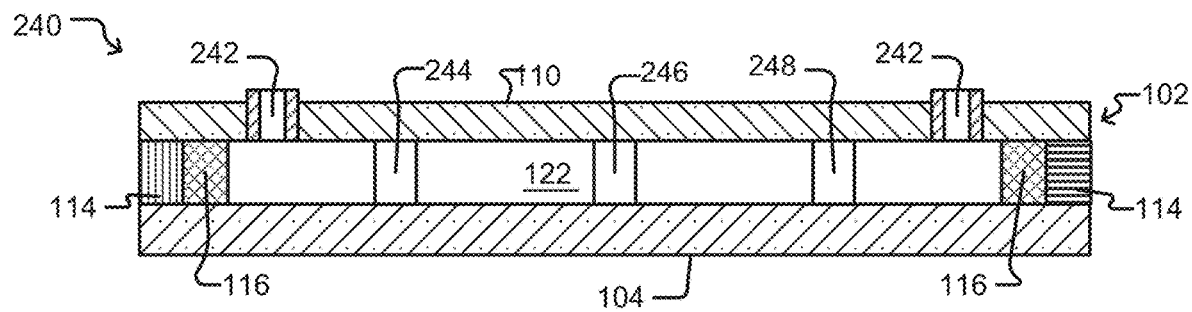
FIGS. 2C and 2D illustrate incubation chambers according to some embodiments of the invention.
Figure 2D:
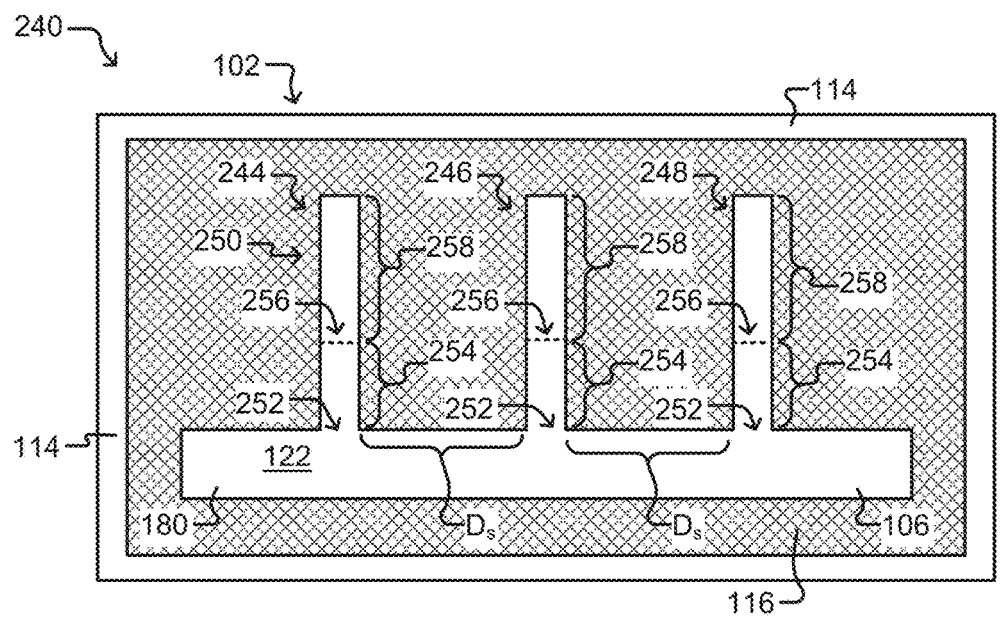

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, an incubation chamber, a flow region, or a flow channel. Furthermore, the microfluidic device 200 may include other fluidic circuit elements. For example, the microfluidic device 200 can include a plurality of growth chambers or incubation chambers and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 nm to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 microns. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Incubation chambers. Non-limiting examples of generic incubation chambers 244, 246, and 248 are shown within the microfluidic device 240 depicted in FIGS. 2C and 2D. Each incubation chamber 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the incubation chamber 244, 246, 248 does not extend into the isolation region 258. Thus, due to the connection region 254, a micro-object (not shown) or other material (not shown) disposed in an isolation region 258 of an incubation chamber 244, 246, 248 can thus be isolated from, and not substantially affected by, a flow of medium 180 in the channel 122.

The channel 122 can thus be an example of a swept region, and the isolation regions 258 of the incubation chambers 244, 246, 248 can be examples of unswept regions. As noted, the channel 122 and incubation chambers 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Prior to introduction of the fluidic medium 180, the microfluidic device may be primed with a gas such as carbon dioxide gas. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
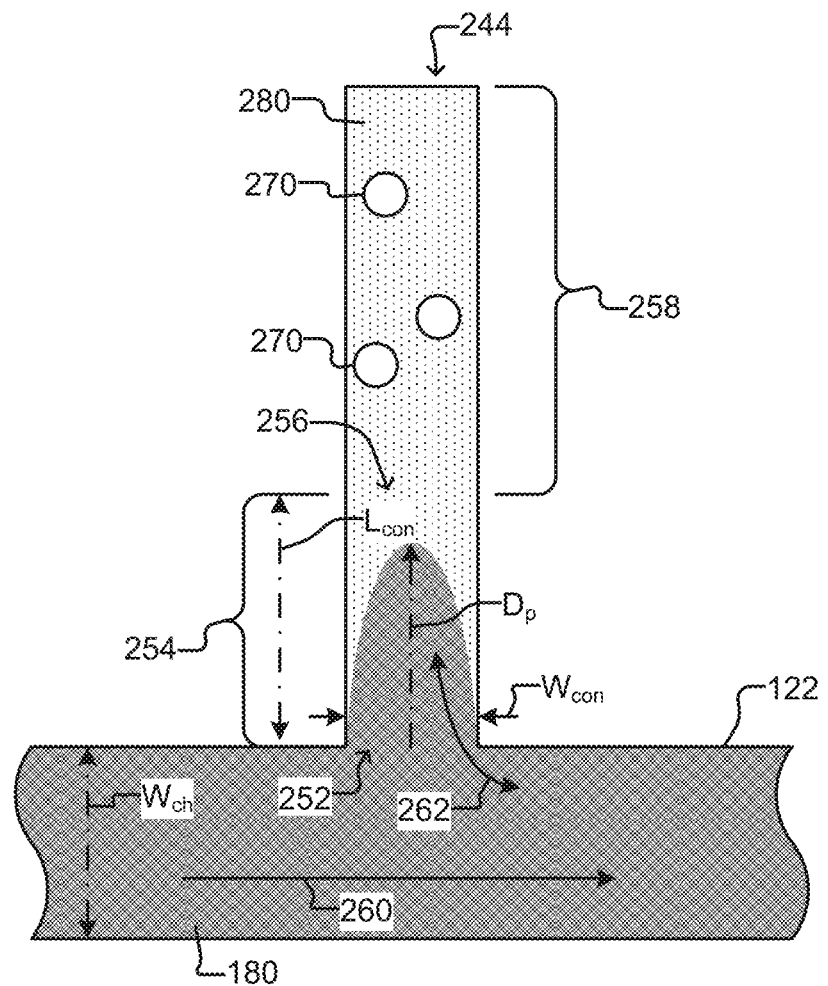
FIG. 2E illustrates a detailed incubation chamber according to some embodiments of the invention.

FIG. 2E illustrates a detailed view of an example of an incubation chamber 244 according to the present invention. Examples of micro-objects 270 are also shown.

As is known, a flow 260 of fluidic medium 180 in a microfluidic channel 122 past a proximal opening 252 of incubation chamber 244 can cause a secondary flow 262 of the medium 180 into and/or out of the incubation chamber 244. To isolate micro-objects 270 in the isolation region 258 of an incubation chamber 244 from the secondary flow 262, the length $L_{con}$ of the connection region 254 of the incubation chamber 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each incubation chamber 244, a maximal velocity Vmax for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity Vmax, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed Vmax, the flow 260 of fluidic medium 180 in the channel 122 will not move miscellaneous particles (e.g., microparticles and/or nanoparticles) from the channel 122 into the isolation region 258 of an incubation chamber 244. Having the length $L_{con}$ of the connection region 254 be greater than the maximum penetration depth $D_p$ of the secondary flow 262 can thus prevent contamination of one incubation chamber 244 with miscellaneous particles from the channel 122 or another incubation chamber (e.g., incubation chambers 246, 248 in FIG. 2D).

Because the channel 122 and the connection regions 254 of the incubation chambers 244, 246, 248 can be affected by the flow 260 of medium 180 in the channel 122, the channel 122 and connection regions 254 can be deemed swept (or flow) regions of the microfluidic device 240. The isolation regions 258 of the incubation chambers 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and incubation chambers 244, 246, 248 can be oriented as follows with respect to the vector of the flow 260 of fluidic medium 180 in the channel 122: the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and incubation chambers 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

Figure 4A:
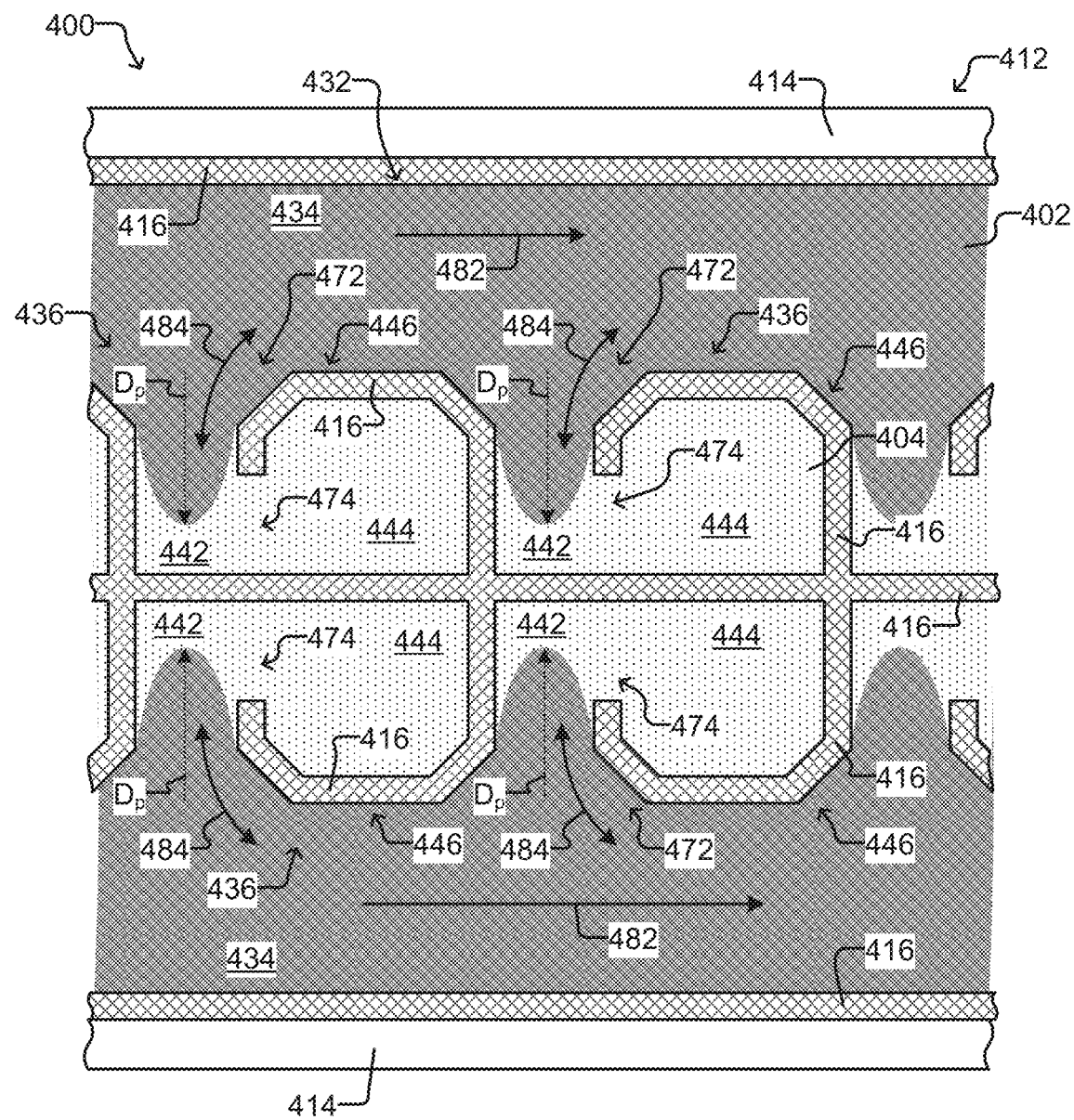
FIGS. 4A-4C show another embodiment of a microfluidic device, including a further example of an incubation chamber used therein.
Figure 4B:
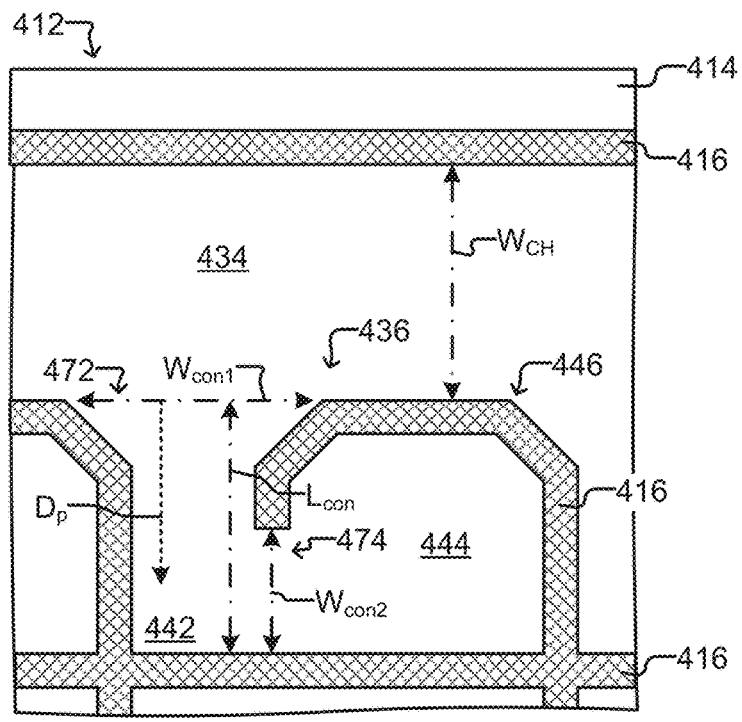
Figure 4C:
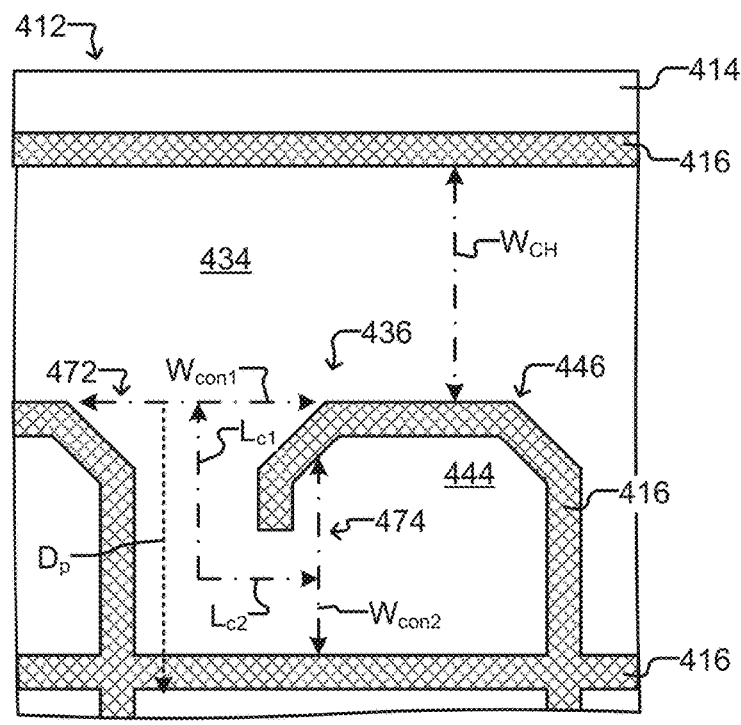

FIGS. 4A-C depict another exemplary embodiment of a microfluidic device 400 containing a microfluidic circuit 432 and flow channels 434, which are variations of the respective microfluidic device 100, circuit 132 and channel 134 of FIG. 1. The microfluidic device 400 also has a plurality of incubation chambers 436 that are additional variations of the above-described incubation chambers 124, 126, 128, 130, 244, 246 or 248. In particular, it should be appreciated that the incubation chambers 436 of device 400 shown in FIGS. 4A-C can replace any of the above-described incubation chambers 124, 126, 128, 130, 244, 246 or 248 in devices 100, 200, 240 and 290. Likewise, the microfluidic device 400 is another variant of the microfluidic device 100, and may also have the same or a different DEP configuration as the above-described microfluidic device 100, 200, 240, 290, as well as any of the other microfluidic system components described herein.

The microfluidic device 400 of FIGS. 4A-C comprises a support structure (not visible in FIGS. 4A-C, but can be the same or generally similar to the support structure 104 of device 100 depicted in FIG. 1), a microfluidic circuit structure 412, and a cover (not visible in FIGS. 4A-C, but can be the same or generally similar to the cover 122 of device 100 depicted in FIG. 1). The microfluidic circuit structure 412 includes a frame 414 and microfluidic circuit material 416, which can be the same as or generally similar to the frame 114 and microfluidic circuit material 116 of device 100 shown in FIG. 1. As shown in FIG. 4A, the microfluidic circuit 432 defined by the microfluidic circuit material 416 can comprise multiple channels 434 (two are shown but there can be more) to which multiple incubation chambers 436 are fluidically connected.

Each incubation chamber 436 can comprise an isolation structure 446, an isolation region 444 within the isolation structure 446, and a connection region 442. From a proximal opening 472 at the channel 434 to a distal opening 474 at the isolation structure 436, the connection region 442 fluidically connects the channel 434 to the isolation region 444. Generally in accordance with the above discussion of FIGS. 2D and 2E, a flow 482 of a first fluidic medium 402 in a channel 434 can create secondary flows 484 of the first medium 402 from the channel 434 into and/or out of the respective connection regions 442 of the incubation chambers 436.

As illustrated in FIG. 4B, the connection region 442 of each incubation chamber 436 generally includes the area extending between the proximal opening 472 to a channel 434 and the distal opening 474 to an isolation structure 446. The length $L_{con}$ of the connection region 442 can be greater than the maximum penetration depth $D_p$ of secondary flow 484, in which case the secondary flow 484 will extend into the connection region 442 without being redirected toward the isolation region 444 (as shown in FIG. 4A). Alternatively, at illustrated in FIG. 4C, the connection region 442 can have a length $L_{con}$ that is less than the maximum penetration depth $D_p$, in which case the secondary flow 484 will extend through the connection region 442 and be redirected toward the isolation region 444. In this latter situation, the sum of lengths $L_1$ and $L_{c2}$ of connection region 442 is greater than the maximum penetration depth $D_p$, so that secondary flow 484 will not extend into isolation region 444. Whether length $L_{con}$ of connection region 442 is greater than the penetration depth $D_p$, or the sum of lengths $L_{c1}$ and $L_{c2}$ of connection region 442 is greater than the penetration depth $D_p$, a flow 482 of a first medium 402 in channel 434 that does not exceed a maximum velocity $V_{max}$ will produce a secondary flow having a penetration depth $D_p$, and micro-objects (not shown but can be the same or generally similar to the micro-objects 270 shown in FIG. 2E) in the isolation region 444 of a incubation chamber 436 will not be drawn out of the isolation region 444 by a flow 482 of first medium 402 in channel 434. Nor will the flow 482 in channel 434 draw miscellaneous materials (not shown) from channel 434 into the isolation region 444 of an incubation chamber 436. As such, diffusion is the only mechanism by which components in a first medium 402 in the channel 434 can move from the channel 434 into a second medium 404 in an isolation region 444 of an incubation chamber 436. Likewise, diffusion is the only mechanism by which components in a second medium 404 in an isolation region 444 of an incubation chamber 436 can move from the isolation region 444 to a first medium 402 in the channel 434. The first medium 402 can be the same medium as the second medium 404, or the first medium 402 can be a different medium than the second medium 404. Alternatively, the first medium 402 and the second medium 404 can start out being the same, then become different, e.g., through conditioning of the second medium by one or more cells in the isolation region 444, or by changing the medium flowing through the channel 434.

As illustrated in FIG. 4B, the width $W_{ch}$ of the channels 434 (i.e., taken transverse to the direction of a fluid medium flow through the channel indicated by arrows 482 in FIG. 4A) in the channel 434 can be substantially perpendicular to a width $W_{con1}$ of the proximal opening 472 and thus substantially parallel to a width $W_{con2}$ of the distal opening 474. The width $W_{con1}$ of the proximal opening 472 and the width $W_{con2}$ of the distal opening 474, however, need not be substantially perpendicular to each other. For example, an angle between an axis (not shown) on which the width $W_{con1}$ of the proximal opening 472 is oriented and another axis on which the width $W_{con2}$ of the distal opening 474 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of incubation chambers (e.g. 124, 126, 128, 130, 244, 246, 248, or 436), the isolation region (e.g. 258 or 444) is configured to contain a plurality of micro-objects. In other embodiments, the isolation region can be configured to contain only one, two, three, four, five, or a similar relatively small number of micro-objects. Accordingly, the volume of an isolation region can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$, $1\times10^7$, $2\times10^7$, $4\times10^7$, $6\times10^7$, $1\times10^8$, cubic microns, or more.

In various embodiments of incubation chambers, the width $W_{ch}$ of the channel 122, 434 at a proximal opening (e.g. 252, 472) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122, 434 can be in other ranges (e.g., a range defined by any of the endpoints listed above). Moreover, the $W_{ch}$ of the channel 122, 434 can be selected to be in any of these ranges in regions of the channel other than at a proximal opening of an incubation chamber.

In some embodiments, an incubation chamber has a cross-sectional height of about 30 to about 200 microns, or about 50 to about 150 microns. In some embodiments, the incubation chamber has a cross-sectional area of about 100,000 to about 2,500,000 square microns, or about 200,000 to about 2,000,000 square microns. In some embodiments, a connection region has a cross-sectional height that matches the cross-sectional height of the corresponding incubation chamber. In some embodiments, the connection region has a cross-sectional width of about 50 to about 500 microns, or about 100 to about 300 microns.

In various embodiments of incubation chambers the height $H_{ch}$ of the channel 122, 434 at a proximal opening 252, 472 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122, 434 can be in other ranges (e.g., a range defined by any of the endpoints listed above). The height $H_{ch}$ of the channel 122, 434 can be selected to be in any of these ranges in regions of the channel other than at a proximal opening of an incubation chamber.

In various embodiments of incubation chambers a cross-sectional area of the channel 122, 434 at a proximal opening 252, 472 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252, 472 can be in other ranges (e.g., a range defined by any of the endpoints listed above).

In various embodiments of incubation chambers, the length $L_{con}$ of the connection region 254, 442 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254, 442 can be in a different range than the foregoing examples (e.g., a range defined by any of the endpoints listed above).

In various embodiments of incubation chambers the width $W_{con}$ of a connection region 254, 442 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254, 442 at a proximal opening 252 can be different than the foregoing examples (e.g., a range defined by any of the endpoints listed above).

In various embodiments of incubation chambers the width $W_{con}$ of a connection region 254, 442 at a proximal opening 252, 472 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only, and the width $W_{con}$ of a connection region 254, 442 at a proximal opening 252, 472 can be different than the foregoing examples (e.g., a range defined by any of the endpoints listed above).

In various embodiments of incubation chambers, a ratio of the length $L_{con}$ of a connection region 254, 442 to a width $W_{con}$ of the connection region 254, 442 at the proximal opening 252, 472 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254, 442 at the proximal opening 252, 472 can be different than the foregoing examples.

In various embodiments of microfluidic devices 100, 200, 240, 290, 400, $V_{max}$ can be set around 0.2, 0.3, 0.4, 0.5, 0.6, 0.7, 0.8, 0.9, 1.0, 1.1, 1.2, 1.3, 1.4, or 1.5 microliters/sec. In some other embodiments, Vmax can be set at about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 microliters/sec. In yet other embodiments, Vmax can be set at or about 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0 or about 9.0 microliters/sec.

In various embodiments of microfluidic devices having incubation chambers, the volume of an isolation region 258, 444 of an incubation chamber can be, for example, at least $3\times10^3$, $6\times10^3$, $9\times10^3$, $1\times10^4$, $2\times10^4$, $4\times10^4$, $8\times10^4$, $1\times10^5$, $2\times10^5$, $4\times10^5$, $8\times10^5$, $1\times10^6$, $2\times10^6$, $4\times10^6$, $6\times10^6$ cubic microns, or more. In various embodiments of microfluidic devices having incubation chambers, the volume of an incubation chamber may be about $5\times10^3$, $7\times10^3$, $1\times10^4$, $3\times10^4$, $5\times10^4$, $8\times10^4$, $1\times10^5$, $2\times10^5$, $4\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some embodiments, the microfluidic device has incubation chambers wherein no more than $1\times10^2$ biological cells may be maintained, and the volume of an incubation chamber may be no more than $2\times10^6$ cubic microns. In some embodiments, the microfluidic device has incubation chambers wherein no more than $1\times10^2$ biological cells may be maintained, and an incubation chamber may be no more than $4\times10^5$ cubic microns. In yet other embodiments, the microfluidic device has incubation chambers wherein no more than 50 biological cells may be maintained, an incubation chamber may be no more than $4\times10^5$ cubic microns.

In various embodiment, the microfluidic device has incubation chambers configured as in any of the embodiments discussed herein where the microfluidic device has about 100 to about 500 incubation chambers; about 200 to about 1000 incubation chambers, about 500 to about 1500 incubation chambers, about 1000 to about 2000 incubation chambers, or about 1000 to about 3500 incubation chambers.

In some other embodiments, the microfluidic device has incubation chambers configured as in any of the embodiments discussed herein where the microfluidic device has about 1500 to about 3000 incubation chambers, about 2000 to about 3500 incubation chambers, about 2500 to about 4000 incubation chambers, about 3000 to about 4500 incubation chambers, about 3500 to about 5000 incubation chambers, about 4000 to about 5500 incubation chambers, about 4500 to about 6000 incubation chambers, about 5000 to about 6500 incubation chambers, about 5500 to about 7000 incubation chambers, about 6000 to about 7500 incubation chambers, about 6500 to about 8000 incubation chambers, about 7000 to about 8500 incubation chambers, about 7500 to about 9000 incubation chambers, about 8000 to about 9500 incubation chambers, about 8500 to about 10,000 incubation chambers, about 9000 to about 10,500 incubation chambers, about 9500 to about 11,000 incubation chambers, about 10,000 to about 11,500 incubation chambers, about 10,500 to about 12,000 incubation chambers, about 11,000 to about 12,500 incubation chambers, about 11,500 to about 13,000 incubation chambers, about 12,000 to about 13,500 incubation chambers, about 12,500 to about 14,000 incubation chambers, about 13,000 to about 14,500 incubation chambers, about 13,500 to about 15,000 incubation chambers, about 14,000 to about 15,500 incubation chambers, about 14,500 to about 16,000 incubation chambers, about 15,000 to about 16,500 incubation chambers, about 15,500 to about 17,000 incubation chambers, about 16,000 to about 17,500 incubation chambers, about 16,500 to about 18,000 incubation chambers, about 17,000 to about 18,500 incubation chambers, about 17,500 to about 19,000 incubation chambers, about 18,000 to about 19,500 incubation chambers, about 18,500 to about 20,000 incubation chambers, about 19,000 to about 20,500 incubation chambers, about 19,500 to about 21,000 incubation chambers, or about 20,000 to about 21,500 incubation chambers.

Figure 2F:
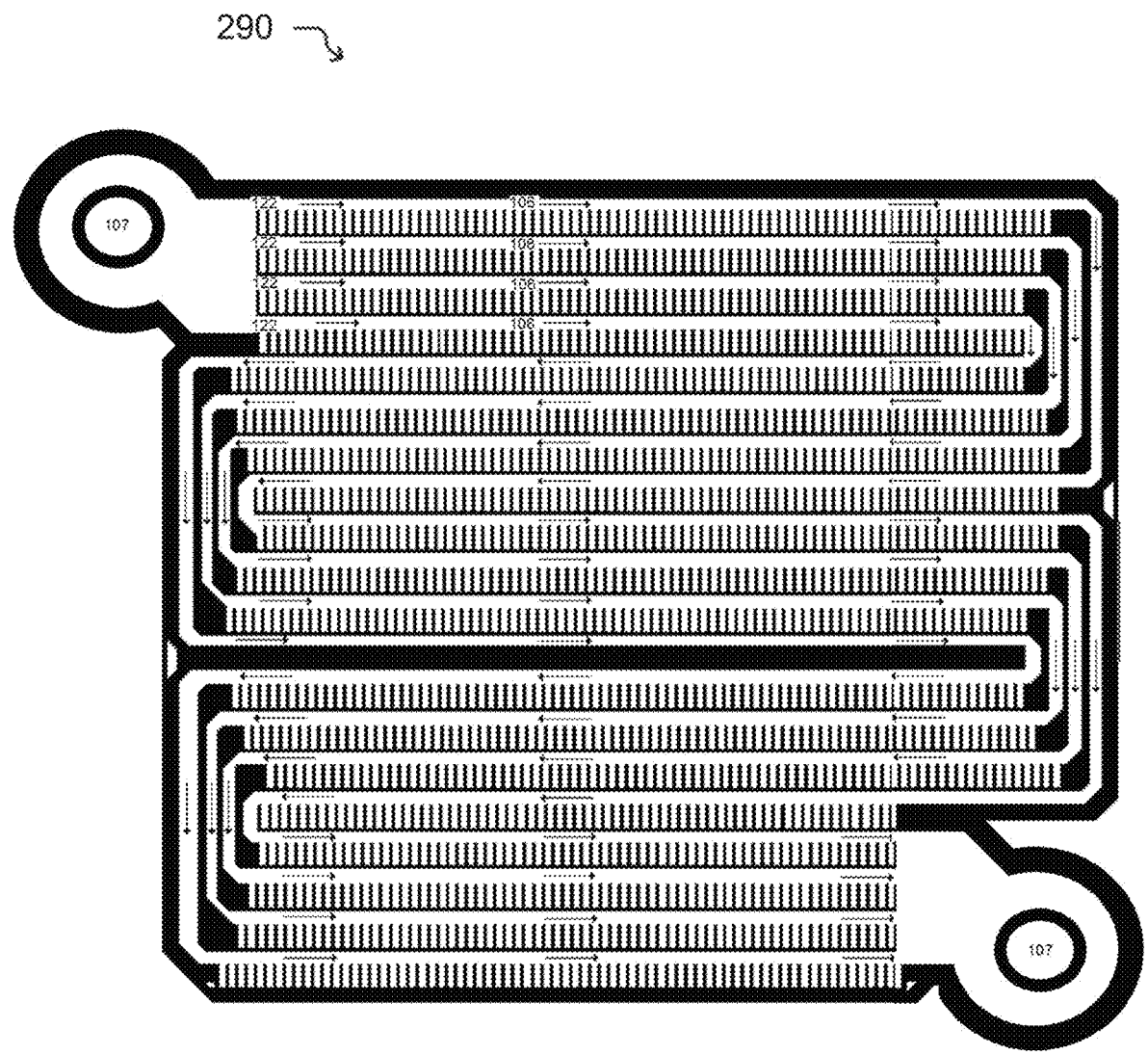
FIG. 2F illustrates a microfluidic device according to an embodiment of the invention.

FIG. 2F illustrates a microfluidic device 290 according to one embodiment. The microfluidic device 290 is illustrated in FIG. 2F is a stylized diagram of a microfluidic device 100. In practice the microfluidic device 290 and its constituent circuit elements (e.g. channels 122 and incubation chambers 128) would have the dimensions discussed herein. The microfluidic circuit 120 illustrated in FIG. 2F has two ports 107, four distinct channels 122 and four distinct flow paths 106. The microfluidic device 290 further comprises a plurality of incubation chambers opening off of each channel 122. In the microfluidic device illustrated in FIG. 2F, the incubation chambers have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
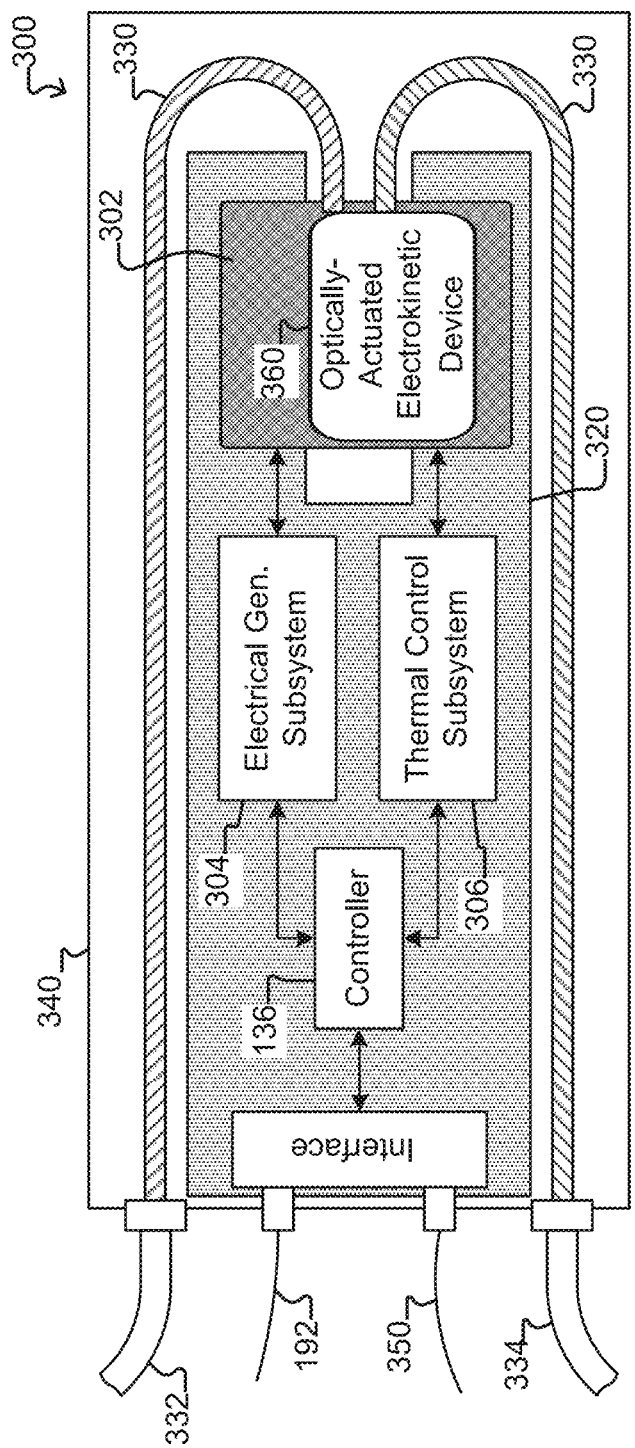
FIG. 3A illustrates a specific example of a system for use with a microfluidic device and associated control equipment according to some embodiments of the invention.
Figure 3B:
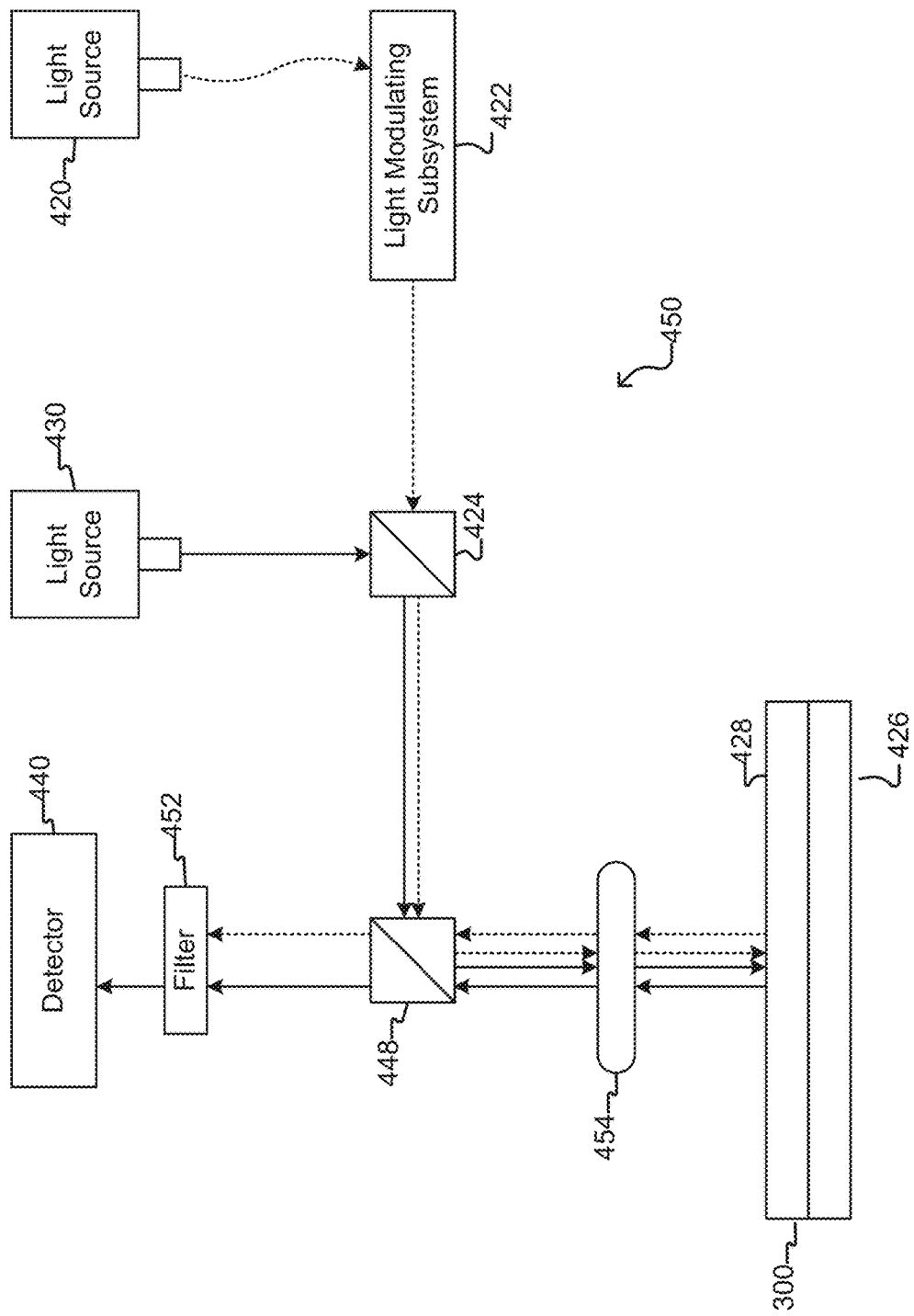
FIG. 3B illustrates an imaging device according to some embodiments of the invention.

FIGS. 3A through 3B shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electrowetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary nest 300 includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to −6.5V power supply generated by a pair of DC-DC converters mounted on the PCBA 320, resulting in a signal of up to 13 Vpp at the microfluidic device 100.

As illustrated in FIG. 3A, the nest 300 can further include a thermal control subsystem 306. The thermal control subsystem 306 can be configured to regulate the temperature of microfluidic device 360 held by the nest 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the nest 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the nest 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI) (not shown), provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 422. The light modulating subsystem 422 can include a digital mirror device (DMD) or a microshutter array system (MSA), either of which can be configured to receive light from a light source 420 and transmits a subset of the received light into an optical train of microscope 450. Alternatively, the light modulating subsystem 422 can include a device that produces its own light (and thus dispenses with the need for a light source 420), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 422 can be, for example, a projector. Thus, the light modulating subsystem 422 can be capable of emitting both structured and unstructured light. One example of a suitable light modulating subsystem 422 is the Mosaic™ system from Andor Technologies™. In certain embodiments, imaging module 164 and/or motive module 162 of system 150 can control the light modulating subsystem 422.

In certain embodiments, the imaging device 194 further comprises a microscope 450. In such embodiments, the nest 300 and light modulating subsystem 422 can be individually configured to be mounted on the microscope 450. The microscope 450 can be, for example, a standard research-grade light microscope or fluorescence microscope. Thus, the nest 300 can be configured to be mounted on the stage 426 of the microscope 450 and/or the light modulating subsystem 422 can be configured to mount on a port of microscope 450. In other embodiments, the nest 300 and the light modulating subsystem 422 described herein can be integral components of microscope 450.

In certain embodiments, the microscope 450 can further include one or more detectors 440. In some embodiments, the detector 440 is controlled by the imaging module 164. The detector 440 can include an eye piece, a charge-coupled device (CCD), a camera (e.g., a digital camera), or any combination thereof. If at least two detectors 440 are present, one detector can be, for example, a fast-frame-rate camera while the other detector can be a high sensitivity camera. Furthermore, the microscope 450 can include an optical train configured to receive reflected and/or emitted light from the microfluidic device 360 and focus at least a portion of the reflected and/or emitted light on the one or more detectors 440. The optical train of the microscope can also include different tube lenses (not shown) for the different detectors, such that the final magnification on each detector can be different.

In certain embodiments, imaging device 194 is configured to use at least two light sources. For example, a first light source 420 can be used to produce structured light (e.g., via the light modulating subsystem 422) and a second light source 430 can be used to provide unstructured light. The first light source 420 can produce structured light for optically-actuated electrokinesis and/or fluorescent excitation, and the second light source 430 can be used to provide bright field illumination. In these embodiments, the motive module 164 can be used to control the first light source 420 and the imaging module 164 can be used to control the second light source 430. The optical train of the microscope 450 can be configured to (1) receive structured light from the light modulating subsystem 422 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 440. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region.

In FIG. 3B, the first light source 420 is shown supplying light to a light modulating subsystem 422, which provides structured light to the optical train of the microscope 450. The second light source 430 is shown providing unstructured light to the optical train via a beam splitter 424. Structured light from the light modulating subsystem 422 and unstructured light from the second light source 430 travel from the beam splitter 424 through the optical train together to reach a second beam splitter 424 (or dichroic filter 448, depending on the light provided by the light modulating subsystem 422), where the light gets reflected down through the objective 454 to the sample plane 428. Reflected and/or emitted light from the sample plane 428 then travels back up through the objective 454, through the beam splitter and/or dichroic filter 448, and to a dichroic filter 452. Only a fraction of the light reaching dichroic filter 452 passes through and reaches the detector 440.

In some embodiments, the second light source 430 emits blue light. With an appropriate dichroic filter 452, blue light reflected from the sample plane 428 is able to pass through dichroic filter 452 and reach the detector 440. In contrast, structured light coming from the light modulating subsystem 422 gets reflected from the sample plane 428, but does not pass through the dichroic filter 452. In this example, the dichroic filter 452 is filtering out visible light having a wavelength longer than 495 nm. Such filtering out of the light from the light modulating subsystem 422 would only be complete (as shown) if the light emitted from the light modulating subsystem did not include any wavelengths shorter than 495 nm. In practice, if the light coming from the light modulating subsystem 422 includes wavelengths shorter than 495 nm (e.g., blue wavelengths), then some of the light from the light modulating subsystem would pass through filter 452 to reach the detector 440. In such an embodiment, the filter 452 acts to change the balance between the amount of light that reaches the detector 440 from the first light source 420 and the second light source 430. This can be beneficial if the first light source 420 is significantly stronger than the second light source 430. In other embodiments, the second light source 430 can emit red light, and the dichroic filter 452 can filter out visible light other than red light (e.g., visible light having a wavelength shorter than 650 nm).

Gaseous Environment.

The system provides a mixture of gases necessary for cell viability, including but not limited to oxygen and carbon dioxide. Both gases dissolve into the fluidic medium, and may be used by the cells, thus altering over time the gas content of the fluidic medium in an isolation region of an incubation chamber. In particular, carbon dioxide content can change over time, which affects the pH of the fluidic media in the microfluidic device. In some experimental conditions, non-optimal oxygen partial pressure may be used.

Flow Controller Providing Perfusion During Incubation.

During the incubating step, the second fluidic medium, present within the isolation region of the incubation chamber may become depleted of nutrients, growth factors or other growth stimulants. The second fluidic medium may accumulate cellular waste products. Additionally, as the at least one biological cell continues to grow during the period of incubation, it may be desirable to alter the nutrients, growth factors or other growth stimulants to be different from those of the first or second media at the start of the incubation. Culturing in an incubation chamber of a microfluidic device as described here may afford the specific and selective ability to introduce and alter chemical gradients sensed by the at least one biological cell, which may much more closely approximate in-vivo conditions. Alternatively, altering the chemical gradients sensed by the at least one biological cell to purposely non-optimized set of conditions may permit cell expansion under conditions designed to explore disease or treatment pathways. The method may therefore include perfusing the first fluidic medium during the incubating step, wherein the first fluidic medium is introduced via at least one inlet 124 of the microfluidic device and wherein the first fluidic medium, optionally comprising components from the second fluidic medium is exported via at least one outlet of the microfluidic device.

Exchange of components of the first fluidic medium, thereby providing fresh nutrients, soluble growth factors, and the like, and/or exchange of waste components of the medium surrounding the cell(s) within the isolation region occurs at the interface of the swept and unswept regions of the incubation chamber substantially under conditions of diffusion. Effective exchange has been surprisingly found to result under substantially no flow conditions. Accordingly, it has been surprisingly found that successful incubation does not require constant perfusion. As result, perfusing may be non-continuous. In some embodiments, perfusing is periodic, and in some embodiments, perfusing is irregular. Breaks between periods of perfusion may be of sufficient duration to permit components of the second fluidic medium in the isolation region to diffuse into the first fluidic medium in the flow channel/region and/or components of the first fluidic medium to diffuse into the second fluidic medium, all without substantial flow of the first medium into the isolation region.

In another embodiment, low perfusion rates may also be employed to obtain effective exchange of the components of fluidic media within and outside of the unswept region of the incubation chamber.

Accordingly, one method of perfusing at least one biological cell in at least one incubation chamber of a microfluidic device is shown in FIG. 5 and includes a perfusing step 5002 where the first fluidic medium is flowed into a flow region fluidically connected to the incubation chamber at a first perfusion rate $R_1$ for a first perfusion time $D_1$ through a flow region of the microfluidic device. $R_1$ may be selected to be a non-sweeping rate of flow, as described herein. Method 500 further includes the step 5004 of stopping the flow of the fluidic medium for a first perfusion stop time $S_1$. Steps 5002 and 5004 are repeated for W repetitions, where W may be an integer selected from 1 to about 1000, whereupon the perfusion process 500 is complete. In some embodiments, W may be an integer of 2 to about 1000.

Figure 6:
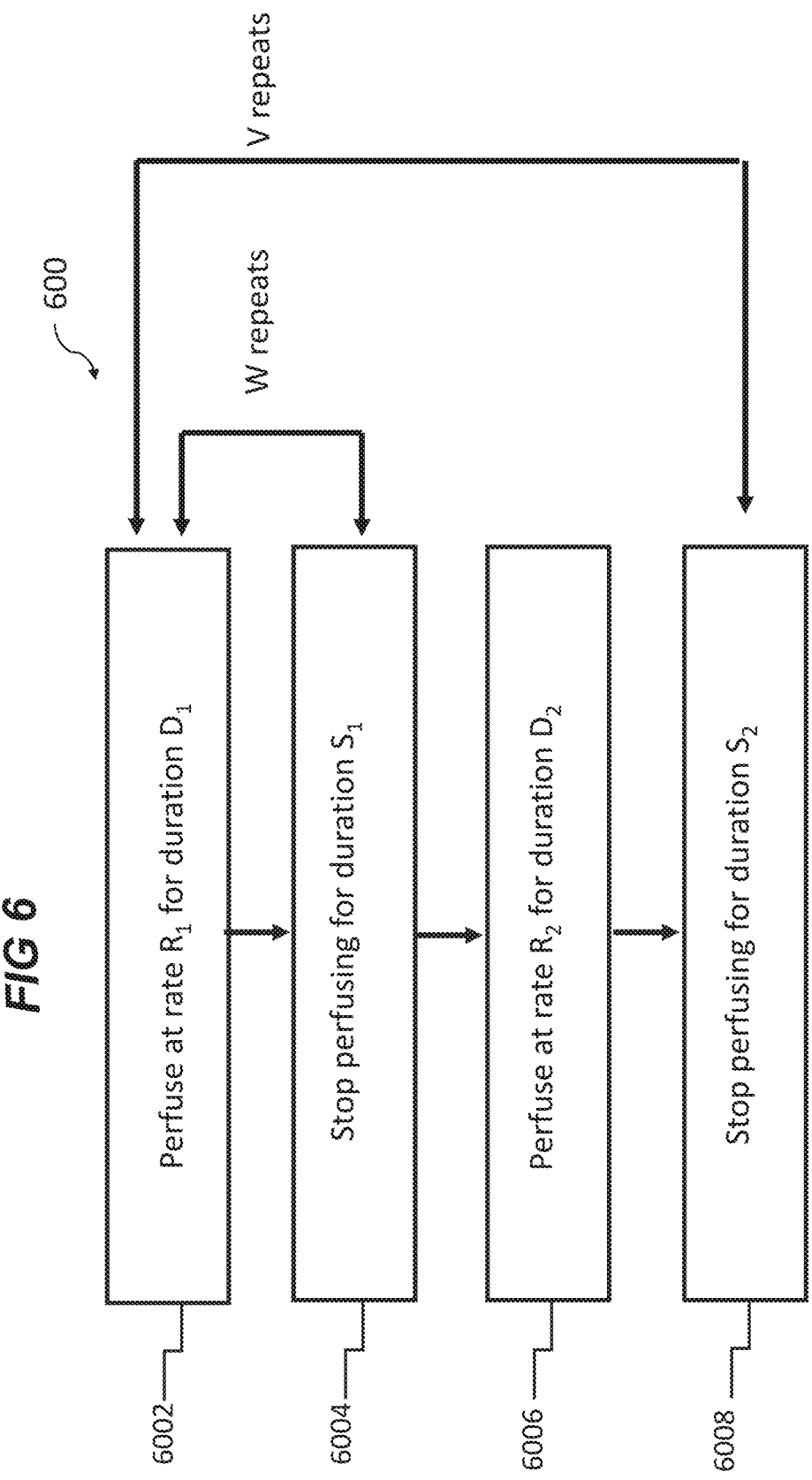
FIG. 6 is an example of another embodiment of a process for perfusing a fluidic medium in a microfluidic device

Another method 600, of perfusing at least one biological cell in at least one incubation chamber of a microfluidic device is shown in FIG. 6, which includes a first perfusion cycle that includes the step 6002 of flowing the fluidic medium into a flow region fluidically connected to the incubation chamber at a first perfusion rate $R_1$ for a first perfusion time $D_1$ through a flow region of the microfluidic device. $R_1$ may be selected to be a non-sweeping rate of flow, as described herein. The first perfusion cycle includes the step 6004 of stopping the flow of the fluidic medium for a first perfusion stop time $S_1$. The first perfusion cycle may be repeated for W repetitions, wherein W is an integer selected from 1 to about 1000. After the Wth repeat of the first perfusion cycle is completed, method 600 further includes a second perfusion cycle, which includes the step 8006 of flowing the first fluidic medium at a second perfusion rate $R_2$ for a second perfusion time $D_2$, wherein $R_2$ is selected to be a non-sweeping rate of flow. The second perfusion cycle of Method 600 further includes the step 6008 of stopping the flow of the fluidic medium for a second perfusion stop time $S_2$. Thereafter, the method returns to step 6002 and 6004 of the first perfusion cycle and the combined two cycle perfusion process is repeated for V repeats, wherein V is an integer of 1 to about 5000. The combination of W and V may be chosen to meet the desired incubation period endpoint In various embodiments of method 500, or 600, perfusing rate $R_1$ may be any non-sweeping rate of flow of fluidic medium as described above for flow controller configurations. In some embodiments, $R_1$ may be about 0.009, 0.010, 0.020, 0.030, 0.040, 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00. 2.10, 2.20, 2.40, 2.50, 2.60, 2.70, 2.80, 2.90 or 3.00 microliters/sec.

In various embodiments of method 600, the second perfusion rate $R_2$ may be any non-sweeping rate of flow of fluidic medium as described as above for flow controller configurations. In some embodiments, the $R_2$ may be 0.009, 0.010, 0.020, 0.030, 0.040, 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00, 2.10, 2.20, 2.40, 2.50, 2.60, 2.70, 2.80, 2.90 or 3.00 microliters/sec. The flow rates $R_1$ and/or $R_2$ may be chosen in any combination. Typically, perfusion rate $R_2$ may be greater than perfusion rate $R_1$, and may be about 5×, 10×, 20×, 30×, 40×, 50×, 60×, 70×, 80×, 90×, 100×, or more than $R_1$. In some embodiments, $R_2$ is at least ten times faster than $R_1$. In other embodiments, $R_2$ is at least twenty times faster than $R_1$. In yet another embodiment, $R_2$ is at least 100× the rate of $R_1$.

In various embodiments of method 500 or 600, first perfusion time $D_1$ may be any suitable duration of perfusion as described above for flow controller configurations. In various embodiments, $D_1$ may be about 5, 10, 15, 20, 25, 30, 35, 40, 45, 50, 55, 60, 65, 70, 80, 90, 100, 110, 120, 130, 140, 150, 160, 170 or 180 sec. In other embodiments, $D_1$ may be a range of time, e.g., about 10 to about 40 sec, as described above. In some embodiments, $D_1$ may be about 30 sec to about 75 sec. In other embodiments, $D_1$ may be about 100 sec. In other embodiments, $D_1$ may be in a range from about 60 sec to about 150 sec. In yet other embodiments, $D_1$ may be about 20 min, 30 min, 40 min, 50 min, 60 min, 80 min, 90 min, 110 min, 120 min, 140 min, 160 min, 180 min, 200 min, 220 min, 240 min, 250 min, 260 min, 270 min, 290 min or 300 min. In some embodiments, $D_1$ is about 40 min to about 180 min.

In various embodiments of method 500 or 600, second perfusion time $D_2$ may be any suitable duration of perfusion as described above for flow controller configurations. In various embodiments, $D_2$ may be about 5 sec, 10 sec, 15 sec, 20 sec, 25 sec, 30 sec, 35 sec, 40 sec, 45 sec, 50 sec, 55 sec, 60 sec, 65 sec, 70 sec, 80 sec, 90 sec or about 100 sec. In other embodiments, $D_2$ may be a range of time, e.g., about 5 sec to about 20 sec, as described above. In other embodiments, $D_2$ may be about 30 sec to about 70 sec. In other embodiments, $D_2$ may be about 60 sec.

In various embodiments of method 500 or 600, the first perfusion time $D_1$ may be the same or different from the second perfusion time $D_2$. $D_1$ and $D_2$ may be chosen in any combination. In some embodiments, the duration of perfusing $D_1$ and/or $D_2$ may be selected to be shorter than the stopping periods $S_1$ and/or $S_2$.

In various embodiments of method 500 or 600, the first perfusion stop time $S_1$ may be selected to be any suitable period of time as described above for an interval of time between periods of perfusion for flow controller configurations. In some embodiments, $S_1$ may be about 0 min, 5 min, about 10 min, about 15 min, about 20 min, about 25 min, about 30 min, about 35 min, about 40 min, about 45 min, about 60 min, about 65 min, about 80 min, about 90 min, about 100 min, about 120 min, about 150 min, about 180 min, about 210 min, about 240 min, about 270 min, or about 300 min. In various embodiments, $S_1$ may be any appropriate range of time, as described above for flow controller configuration intervals between perfusion, e.g. about 20 to about 60 min. In some embodiments, $S_1$ may be about 10 min to about 30 min. In other embodiments, $S_1$ may be about 15 min. In yet other embodiments, $S_1$ may be about 0 sec, 5 sec, 10 sec, 20 sec, 30 sec, 40 sec, 50 sec, 60 sec, 70 sec, 80 sec, or about 90 sec. In some embodiments, $S_1$ is about 0 sec.

In various embodiments of method 500 or 600, the second perfusion stop time $S_2$ may be selected to be any suitable period of time as described above for an interval of time between periods of perfusion for flow controller configurations. In some embodiments, $S_2$ may be about 0 min, 5 min, about 6 min, about 7 min, about 8 min, about 9 min, about 10 min, about 20 min, about 30 min, about 45 min, about 50 min, about 60 about 90 min, about 120 min, about 180 min, about 240 min, about 270 min, or about 300 min. In various embodiments, $S_2$ may be any appropriate range of time, as described above for flow controller configuration intervals between perfusion, e.g. about 15 to about 45 min. In some embodiments, $S_2$ may be about 10 min to about 30 min. In other embodiments, $S_2$ may be about 8 min or 9 min. In other embodiments, $S_2$ is about 0 min.

In various embodiments of method 500 or 600, the first perfusion stop time $S_1$ and the second perfusion stop time $S_2$ may be selected independently from any suitable value. $S_1$ may be the same or different from $S_2$.

In various embodiments of method 500 and 600, the number of W repetitions may be selected to be the same or different from the number of V repetitions.

In various embodiments of methods 500 or 600, W may be about 1, about 4, about 5, about 6, about 8, about 10, about 12, about 15, about 18, about 20, about 24, about 30, about 36, about 40, about 45, or about 50. In some embodiments, W may be selected to be about 1 to about 20. In some embodiments, W may be 1.

In various embodiments of method 600, V may be about 5, about 10, about 20, about 25, about 30, about 35, about 40, about 50, about 60, about 80, about 100, about 120, about 240, about 300, about 350, about 400, about 450, about 500, about 600, about 750, about 900, or about 1000. In some embodiments, V may be selected to be about 10 to about 120. In other embodiments, V may be about 5 to about 24. In some embodiments, V may be about 30 to about 50 or may be about 400 to about 500.

In various embodiments of method 600, the number of W repetitions may be selected to be the same or different from the number of V repetitions.

In various embodiments of methods 500 or 600 a total time for the first step of perfusing (represented by steps 5002/5004 or 6002/6004) is about 1 h to about 10 h and W is an integer is 1. In various embodiments, the total time for the first step of perfusing is about 9 min to about 15 min.

In various embodiments of method 600, a total time for the second step of a perfusing cycle (represented by step 6006/6008) is about 1 min to about 15 min or about 1 min to about 20 min.

In any of methods 500 or 600, the perfusing method may be continued for the entire incubation period of the biological cell, e.g., for about 1, about 2, about 3, about 4, about 5, about 6, about 7, about 8 about 9, about 10 days or more.

In another non-limiting embodiment of method 600 of FIG. 6, the controller may be configured to perfuse the fluidic medium(s) in the flow region having longer periods of perfusion $D_1$ during the perfusing step 6002. The controller may perfuse the fluidic medium at a first rate for a period of about 45 min, about 60 min, about 75 min, about 90 min, about 105 min, about 120 min, about 2.25 h, about 2.5 h, about 2.45 h, about 3.0 h, about 3.25 h, about 3.5 h, about 3.75 h, about 4.0 h, about 4.25 h, about 4.5 h, about 4.75 h, about 5 h, or about 6 h. At the end of the first perfusion period $D_1$, the flow of the fluidic medium may be stopped for a stopping period of time $S_1$, which may be about 0 sec, 15 sec, 30 sec, about 45 sec, about 1 min, about 1.25 min, about 1.5 min, about 2.0 min, about 3.0 min, about 4 min, about 5 min or about 6 min. In some embodiments, the first flow rate $R_1$ may be selected to be about 0.009, 0.01, 0.02, 0.03, 0.05, 0.1, 0.2, 0.3, 0.4, or about 0.5 microliters/sec. The flow of the fluidic medium may be stopped for a perfusion stopping period $S_1$ of less than about 1 minute or $S_1$ may be 0 sec. Alternatively, $S_1$ may be about 30 sec, about 1.5 min, about 2.0 min, about 2.5 min, or about 3 min. A second perfusion period $D_2$ may follow, using a different perfusion rate. In some embodiments, the second perfusion rate may be higher than the first perfusion rate. In some embodiments, the second perfusion rate $R_2$ may be selected from about 1.0, 1.1, 1.2, 1.3, 1.4, 1.5, 1.7, 1.9, 2.0, 2.2, 2.4, 2.6, 2.8, 3.0, 3.2, 3.4, 3.6, 3.8, 4.0, 4.2, 4.4, 4.6, 4.8, 5.0, 6.0, 7.0, 8.0 or about 9.0 microliters/sec. The second perfusion period $D_2$ may for about 1 sec, about 2 sec, about 3 sec, about 4 sec, about 5 sec, about 6 sec, about 10 sec, about 15 sec, about 30 sec, about 45 sec, about 60 sec, about 65 sec, about 75 sec, about 80 sec, or about 90 sec. Perfusing may be then stopped for a second perfusion stop period $S_2$, which may be about 0 sec, 10 sec, about 20 sec, about 30 sec, about 40 sec, about 50 sec, about 60 sec, about 1.5 min, about 1.75 min, about 2.0 min, about 2.5 min, about 2.75 min, about 3.0 min or about 4.0 min. In some embodiments, $D_1$ may be about 2 h, about 3 h, or about 4 h. In various embodiments, $D_1$ may be about 4 h. In various embodiments, $S_1$ may be 0 sec or less than about one minute. The second perfusion period $D_2$ may be about 1 sec to about 6 sec. In some embodiments, the second perfusion stop period $S_2$ may be about 40 sec to about 1.5 min.

Accordingly, a method is provided for perfusing at least one biological cell in at least one incubation chamber of a microfluidic device including the steps of: perfusing the at least one biological cell using a first perfusion step including: flowing a first fluidic medium at a first perfusion rate $R_1$ for a first perfusion time $D_1$ through a flow region of the microfluidic device, where the flow region is fluidically connected to the incubation chamber, wherein $R_1$ is selected to be a non-sweeping rate of flow; stopping the flow of the first fluidic medium for a first perfusion stop time $S_1$; and repeating the first perfusion step for W repetitions, where W is an integer selected from 1 to 1000. The method may further include a step of perfusing the at least one biological cell using a second perfusion step comprising: flowing the first fluidic medium at a second perfusion rate $R_2$ for a second perfusion time $D_2$, where $R_2$ is selected to be a non-sweeping rate of flow; stopping the flow of the first fluidic medium for a second perfusion stop time $S_2$; and repeating the first perfusion step followed by the second perfusion step for V repetitions, wherein V is an integer of 1 to 1000.

The second perfusion rate $R_2$ may be greater than the first perfusion rate $R_1$. The first perfusion time $D_1$ may be the same or different from the second perfusion time $D_2$. The first perfusion stop time $S_1$ may be the same or different from the second perfusion stop time $S_2$. The number of W repetitions may be the same or different from the number of V repetitions, when the second perfusing step is performed. $R_2$ may be at least ten times faster than $R_1$. Alternatively, $R_2$ may be at least twenty times faster than $R_1$. $R_2$ may be at least 100 times as fast as $R_1$. $D_1$ may be about 30 sec to about 75 sec. In other embodiments, $D_1$ may be about 40 min to about 180 min or about 180 min to about 300 min. In some other embodiments, $D_1$ may be about 60 sec to about 150 sec. $S_1$ may be about 10 min to about 30 min. In other embodiments, $S_1$ may be about 5 min to about 10 min. In yet other embodiments, $S_1$ may be zero. In some embodiments, $D_1$ may be about 40 min to about 180 min, and $S_1$ may be zero. In other embodiments, $D_1$ may be about 60 sec to about 150 sec, and $S_1$ may be about 5 min to about 10 min. In yet other embodiments, $D_1$ may be about 180 min to about 300 min, and $S_1$ may be zero. The total time for the first perfusing step may be about 1 h to about 10 h. In other embodiments, the total time for the first perfusing step may be about 2 h to about 4 h. In some embodiments, W may be an integer greater than 2. In some embodiments, W may be about 1 to about 20. In some embodiments, $D_2$ may be about 10 sec to about 25 sec. In other embodiments, $D_2$ may be about 10 sec to about 90 sec. In some embodiments, $S_2$ may be about 10 min to about 30 min. In other embodiments, $S_2$ may be about 15 min. In some embodiments, V may be about 10 to about 120. In some embodiments, V may be about 30 to about 50 or may be about 400 to about 500. In some embodiments, $D_2$ may be about 1 sec to about 6 sec. and $S_2$ may be 0 sec. In some embodiments, $D_2$ may be about 10 sec to about 90 sec and $S_2$ may be about 40 sec to about 1.5 min. In some embodiments, a total time for one repeat of the second perfusing step may be about 1 min to about 15 min.

Temperature Control.

In some embodiments, the at least one conditioned surface of the incubation chamber(s) and/or flow region(s) is conditioned by controlling the temperature of the at least one conditioned surface. The system may include a component that can control and modulate the temperature of the at least one conditioned surface of the incubation chambers and/or flow regions of the microfluidic device. The system may include Peltier heating, resistive heating, or any other suitable method for providing temperature modulation to the microfluidic device. The system may also include sensors and/or feedback components to control heat input to a predetermined range. In some embodiments, the at least one conditioned surface has a temperature of at least about 25° C., 26° C., 27° C., 28° C., 29° C., 30° C., 31° C., 32° C., 33° C., 34° C., 35° C., 36° C., 37° C., 38° C., 39° C., or about 40° C. In some embodiments, the at least one surface has a temperature greater than about 25° C. In other embodiments, the at least one surface has a temperature in the range from about 30°-40° C.; about 35° C. to about 38° C.; or about 36° C. to about 37° C. In some embodiments, the at least one conditioned surface has a temperature of at least about 30° C.

Conditioned Surface of the Microfluidic Device.

In some embodiments, at least one surface of the microfluidic device is conditioned to support cell growth, viability, portability, or any combination thereof. In some embodiments, substantially all the inner surfaces are conditioned. A conditioned surface may be one of the elements facilitating successful cell incubation within the microfluidic device. Identification of an appropriate conditioned surface may require balancing a number of operational requirements. First, the conditioned surface may provide a contacting surface that acts to shield cells from the types of materials which may be used in the fabrication of microfluidic devices of this class. Without being limited by theory, the conditioned surface may be surrounded by waters of hydration, which provide an aqueous, not a metallic contact layer with the cells. Second, the conditioned surface may provide a contacting surface with which the at least one biological cell may be supported adequately during incubation, without substantially inhibiting the ability of the cell to be removed from the incubation chamber after completion of incubation. For example, many cells require a contacting surface to have some degree of hydrophilicity in order to adhere sufficiently to be viable and/or grow. Alternatively, some cells may require a contacting surface having a degree of hydrophobicity in order to grow and present desired levels of viability. Additionally, some cells may require the presence of selected proteins or peptide motifs within the contacting surface in order to initiate viability/growth responses. Third, the conditioning of the at least one surface may permit the motive forces used in the microfluidic device to function substantially within normal functioning power range. For example, if light actuated motive forces are employed, the conditioned surface may substantially permit passage of light through the conditioned surface such that the light actuated motive force is not substantially inhibited.

The at least one conditioned surface may include a surface of the incubation chamber or a surface of the flow region, or a combination thereof. In some embodiments, each of a plurality of incubation chambers has at least one conditioned surface. In other embodiments each of a plurality of flow regions has at least one conditioned surface. In some embodiments, at least one surface of each of a plurality of incubation chambers and each of a plurality of flow regions are conditioned surfaces.

Conditioned Surface Including a Polymer.

The at least one conditioned surface may include a polymer. The polymer may be covalently or non-covalently linked to the at least one surface. Polymers may have a variety of structural motifs, including block polymers (and copolymers); star polymers (star copolymers); and graft or comb polymers (graft copolymers), all of which may be suitable for use herein.

The polymer may include a polymer including alkylene ether moieties. A wide variety of alkylene ether containing polymers may be suitable for use in the microfluidic device described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers range in average molecular mass $M_w$ from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a conditioned surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

In other embodiments, the polymer conditioned surface may include a polymer containing carboxylic acid moieties. The carboxylic acid subunit may be an alkyl, alkenyl or aromatic moiety containing subunit. One non-limiting example is polylactic acid (PLA).

In some other embodiments, the polymer conditioned surface may include a polymer containing urethane moieties, such as, but not limited to polyurethane.

In other embodiments, the polymer conditioned surface may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. These latter exemplary polymers are polyelectrolytes and may alter the characteristics of the surface to aid/deter adhesion.

In yet other embodiments, the polymer conditioned surface may include a polymer containing phosphate moieties, either at a terminus of the polymer backbone or pendant from the backbone of the polymer.

In yet other embodiments, the polymer conditioned surface may include a polymer containing saccharide moieties.

In a non-limiting example, polysaccharides such as those derived from algal or fungal polysaccharides such as xanthan gum or dextran may be suitable to form a polymer conditioned surface which may aid or prevent cell adhesion. For example, a dextran polymer having a size about 3 Kda may be used to provide a conditioned surface within a microfluidic device.

In yet other embodiments, the polymer conditioned surface may include a polymer containing nucleotide moieties, i.e. a nucleic acid, which may have ribonucleotide moieties or deoxyribonucleotide moieties. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation. A nucleic acid containing polymer may include a polyelectrolyte which may aid or prevent adhesion.

In yet other embodiments, the polymer conditioned surface may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA). In some embodiments, an extracellular matrix (ECM) protein may be provided within the conditioned surface for optimized cell adhesion to foster cell growth. A cell matrix protein which may be included in a conditioned surface can include, but is not limited to, a collagen, an elastin, an RGD-containing peptide (e.g. a fibronectin), or a laminin. In yet other embodiments, growth factors, cytokines, hormones or other cell signaling species may be provided within the at least one conditioned surface of the microfluidic device.

In further embodiments, the polymer conditioned surface may include a polymer including amine moieties. The polyamino polymer may include a natural polyamine polymer or a synthetic polyamine polymer. Examples of natural polyamines include spermine, spermidine, and putrescine.

In some embodiments, the polymer conditioned surface may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the conditioned surface.

Covalently Linked Conditioned Surface.

In some embodiments, the at least one conditioned surface includes a covalently linked moiety configured to support cell growth, viability, portability, or any combination thereof of the one or more biological cells within the microfluidic device. The covalently linked moiety can include a linking group, wherein the linking group is covalently linked to a surface of the microfluidic device. The linking group is also linked to the moiety configured to support cell growth, viability, portability, or any combination thereof of the one or more biological cells within the microfluidic device. The surface to which the linking group links may include a surface of the substrate of the microfluidic device, which for embodiments in which the microfluidic device includes a DEP configuration, can include silicon and/or silicon dioxide. In some embodiments, the covalently linked conditioned surface includes all of the inner surfaces of the microfluidic device.

Figure 7:
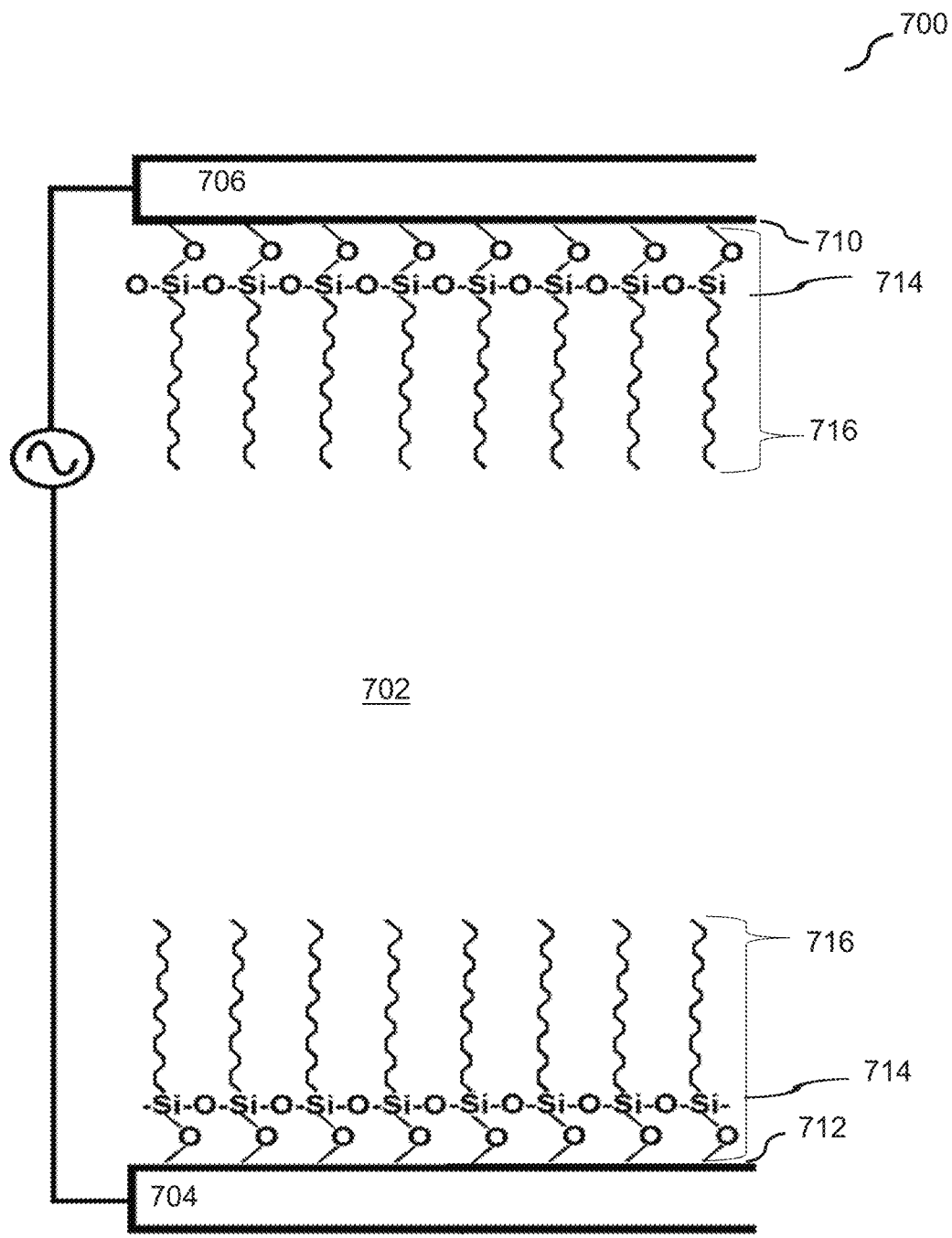
FIG. 7 is a schematic representation of a conditioned surface providing enhanced support cell growth, viability, portability, or any combination thereof This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

A schematic representation is shown in FIG. 7 for a microfluidic device having a conditioned surface. As seen in FIG. 7, a microfluidic device 700 has a first DEP substrate 704 and a second DEP substrate 706 facing an enclosed region 702 of the microfluidic device which may include the at least one incubation chamber and/or the flow region. The device 700 may be otherwise configured like any of microfluidic devices 100, 200, 240, 290, 400, 500A-E, or 600. The enclosed region 702 may be the region in which biological cells are either maintained or are imported into or exported out from. The inner surfaces 710 (of the second DEP substrate 706) and 712 (of the first DEP substrate 704) are modified with a conditioned surface 716, which may be any moiety supporting cell growth, viability, portability, or any combination thereof. The conditioned surface is covalently linked to oxide functionalities of the inner surfaces via a siloxy linking group 714 in this embodiment.

In some embodiments, the covalently linked moiety configured to support cell growth, viability, portability, or any combination thereof, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

The covalently linked moiety configured to support cell growth, viability, portability, or any combination thereof of one or more biological cells within the microfluidic device may be any polymer as described herein, and may include one or more polymers containing alkylene oxide moieties, carboxylic acid moieties, saccharide moieties, sulfonic acid moieties, phosphate moieties, amino acid moieties, nucleic acid moieties, or amino moieties.

In other embodiments, the covalently linked moiety configured to support cell growth, viability, portability, or any combination thereof of one or more biological cells may include non-polymeric moieties such as an alkyl moiety, fluoroalkyl moiety (including but not limited to perfluoroalkyl), amino acid moiety, alcohol moiety, amino moiety, carboxylic acid moiety, phosphonic acid moiety, sulfonic acid moiety, sulfamic acid moiety, or saccharide moiety.

In some embodiments, the covalently linked moiety may be an alkyl group. The alkyl group can comprise carbon atoms that form a linear chain (e.g., a linear chain of at least 10 carbons, or at least 14, 16, 18, 20, 22, or more carbons). Thus, the alkyl group may be an unbranched alkyl. In some embodiments, the alkyl group may include a substituted alkyl group (e.g., some of the carbons in the alkyl group can be fluorinated or perfluorinated). The alkyl group may comprise a linear chain of substituted (e.g., fluorinated or perfluorinated) carbons joined to a linear chain of non-substituted carbons. For example, the alkyl group may include a first segment, which may include a perfluoroalkyl group, joined to a second segment, which may include a non-substituted alkyl group. The first and second segments may be joined directly or indirectly (e.g., by means of an ether linkage). The first segment of the alkyl group may be located distal to the linking group, and the second segment of the alkyl group may be located proximal to the linking group. In other embodiment, the alkyl group may include a branched alkyl group and may further have one or more arylene group interrupting the alkyl backbone of the alkyl group. In some embodiments, a branched or arylene-interrupted portion of the alkyl or fluorinated alkyl group is located at a point distal to the covalent linkage to the surface.

In other embodiments, the covalently linked moiety may include at least one amino acid, which may include more than one amino acids. The covalently linked moiety may include a peptide or a protein. In some embodiments, the covalently linked moiety may include an amino acid which may provide a zwitterionic surface to support cell growth, viability, portability, or any combination thereof.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the incubation chamber.

The covalently linked moiety may include one or more carboxylic acid, phosphonic acid, sulfamic or sulfonic acid moieties. In some embodiments, the covalently linked moiety may include one or more nucleic acid moieties, which may have a sequence of individual nucleotides that is designed to capture nucleic acids from biological cells within the microfluidic device. The capture nucleic acids may have a nucleotide sequence that is complementary to the nucleic acid from the biological cells and may capture the nucleic acid by hybridization.

The conditioned surface may be composed of only one kind of moiety or may include a more than one different kind of moiety. For example, the fluoroalkyl conditioned surfaces (including perfluoroalkyl) may have a plurality of covalently linked moieties which are all the same, e.g. has the same covalent attachment to the surface and has the same number of fluoromethylene units comprising the fluoroalkyl moiety supporting growth and/or viability and/or portability. Alternatively, the conditioned surface may have more than one kind of moiety attached to the surface. For example, the conditioned surface may include alkyl or fluoroalkyl groups having a specified number of methylene or fluoromethylene units and may further include a further set of groups attached to the surface having a charged moiety attached to an alkyl or fluoroalkyl chain that has a greater number of methylene or fluoromethylene units. In some embodiments, the conditioned surface having more than one kind of moiety attached may be designed such that a first set of attached ligands which have a greater number of backbone atoms and thus having a greater length from the covalent attachment to the surface, may provide capacity to present bulkier moieties at the conditioned surface, while a second set of attached ligands having different, less sterically demanding termini while having fewer backbone atoms can help to functionalize the entire substrate surface to prevent undesired adhesion or contact with a silicon or alumina substrate itself. In another example, the moieties attached to the surface may provide a zwitterionic surface presenting alternating charges in a random fashion on the surface. Methods of preparing these surfaces may be found in the cross-referenced U.S. patent application Ser. No. 15/135,707, filed on Apr. 22, 2016.

Conditioned Surface Properties.

In some embodiments, the covalently linked moieties may form a monolayer when covalently linked to the surface of the microfluidic device (e.g., a DEP configured substrate surface). In some embodiments, the conditioned surface formed by the covalently linked moieties may have a thickness of less than 10 nm (e.g., less than 5 nm, or about 1.5 to 3.0 nm). In other embodiments, the conditioned surface formed by the covalently linked moieties may have a thickness of about 10 nm to about 50 nm. In some embodiments, the conditioned surface does not require a perfectly formed monolayer to be suitably functional for operation within a DEP configuration.

Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). The physical thickness and uniformity of the conditioned surface can be measured using an ellipsometer.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Various properties for conditioned surfaces which may be used in DEP configurations are included in the table below. As can be seen, for entries 1 to 7, which were all covalently linked conditioned surfaces as described herein, the thickness as measured by ellipsometry were consistently thinner than that of entry 8, a CYTOP surface which was formed by non-covalent spin coating (N/A represents data not available throughout the table). Fouling was found to be more dependent upon the chemical nature of the surface than upon the mode of formation as the fluorinated surfaces were typically less fouling than that of alkyl (hydrocarbon) conditioned surfaces

TABLE 1

Properties of various conditioned surfaces prepared by covalently modifying a surface, compared to CYTOP, a non-covalently formed surface.

| Surface modification type | Formula of surface modifying reagent | Thickness | Fouling |
|---|---|---|---|
| Alkyl terminated siloxane ($C_{16}$) | $CH_3$—$(CH_2)_{15}$—Si—$(OCH_3)_3$ | N/A | More fouling than fluorinated layers. |
| Alkyl terminated siloxane ($C_{18}$) | $CH_3$—$(CH_2)_{17}$—Si—$(OCH_3)_3$ | ~2 nm | More fouling than fluorinated layers. |
| Alkyl-terminated phosphonate ester $C_{18}P$ | $CH_3$—$(CH_2)_{17}$—P=O(OH)$_2$ | N/A | More fouling than fluorinated layers. |
| Alkyl terminated siloxane ($C_{22}$) | $CH_3$—$(CH_2)_{21}$—Si—$(OCH_2CH_3)_3$ | ~2-2.5 nm | More fouling than fluorinated layers. |
| Fluoroalkyl-terminated alkyl-siloxane $C_{10}F$ | $CF_3$—$(CF_2)_7$—$(CH_2)_2$—Si—$(OCH_3)_3$ | ~1 nm | More resistant to fouling than alkyl-terminated layers |
| Fluoroalkyl-terminated alkyl-siloxane ($C_{16}F$) | $CF_3$—$(CF_2)_{13}$—$(CH_2)_2$—Si—$(OCH_3)_3$ | ~2 nm | More resistant to fouling than alkyl-terminated layers |
| Fluoroalkyl-terminated alkoxy-alkyl-siloxane $C_6FC_{13}$ | $CF_3$—$(CF_2)_5$—$(CH_2)_2$—O—$(CH_2)_{11}$—Si(OCH$_3$)$_3$ | ~2 nm | N/A |
| CYTOP Fluoro-polymer [1,2] | | ~30 nm | More resistant to fouling than alkyl-terminated layers |

[1] CYTOP structure:

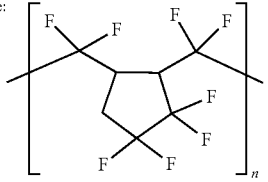

[2] Spin coated, not covalent.

Linking Group to Surface.

The covalently linked moieties forming the conditioned surface are attached to the surface via a linking group. The linking group may be a siloxy linking group formed by the reaction of a siloxane containing reagent with oxides of the substrate surface, which may be formed from silicon or aluminum oxide. In some other embodiments, the linking group may be a phosphonate ester formed by the reaction of a phosphonic acid containing reagent with the oxides of the silicon or aluminum substrate surface.

Multi-Part Conditioned Surface.

The covalently linked conditioned surface may be formed by reaction of a surface conditioning reagent which is configured to already contain the moiety providing the conditioned surface (e.g., an alkyl siloxane reagent or a fluoro substituted alkyl siloxane reagent, which may include a perfluoroalkyl siloxane reagent), as is described below. Alternatively, the conditioned surface may be formed by coupling the moiety which supports cell growth, viability, portability, or any combination thereof to a surface modifying ligand that itself is covalently linked to the surface.

Structures for a Conditioned Surface and Methods of Preparation.

In some embodiments, a conditioned surface covalently linked to oxides of the surface of the dielectrophoresis substrate has a structure of Formula 1:

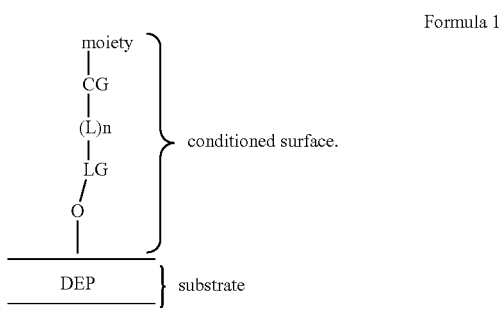

Formula 1

The conditioned surface may be linked covalently to oxides of the surface of the dielectrophoresis substrate. The dielectrophoresis substrate may be silicon or alumina, and oxides may be present as part of the native chemical structure of the substrate or may be introduced as discussed below. The conditioned surface may be attached to the oxides via a linking group LG which may be a siloxy or phosphonate ester group, formed from the reaction of a siloxane or phosphonic acid group with the oxides.

The moiety configured to support cell growth, viability, portability, or any combination thereof, may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids. An alkyl or fluoroalkyl moiety may have a backbone chain length of equal to or greater than 10 carbons. In some embodiments, the alkyl or fluoroalkyl moiety may have a backbone chain length of about 10, 12, 14, 16, 18, 20, or 22 carbons.

The linking group LG may be directly or indirectly connected to the moiety providing support cell growth, viability, portability, or any combination thereof within the microfluidic device. When the linking group LG is directly connected to the moiety, optional linker L is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties selected from the group consisting of ether, amino, carbonyl, amido, or phosphonate groups, in some non-limiting examples. Additionally, the linker L may have one or more arylene, heteroarylene, or heterocyclic groups interrupting the backbone of the linker. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms. In other embodiments, the backbone atoms are not all carbons, and may include any possible combination of silicon, carbon, nitrogen, oxygen, sulfur or phosphorus atoms, subject to chemical bonding limitations as is known in the art.

In some embodiments, the moiety supporting cell growth, viability, portability, or any combination thereof may be added to the surface of the substrate in a multi-step process. When the moiety is coupled to the surface in a step wise fashion, the linker L may further include a coupling group CG, as shown in Formula 2.

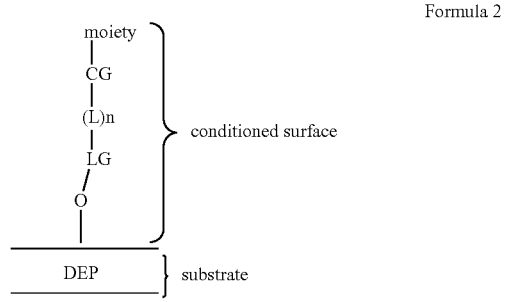

Formula 2

For Formula 2, the moiety configured to support cell growth, viability, portability or any combination thereof, linker L, and linking group LG may be as defined for Formula 1. In some embodiments, the coupling group CG represents the resultant moiety from reaction of a reactive moiety Rx and a moiety that it is configured to react with, a reactive pairing moiety $R_{px}$. For example, one typical CG may include a carboxamidyl group, which is the result of the reaction of an amino group with a derivative of a carboxylic acid, such as an activated ester, an acid chloride or the like. CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end of the linker L, where the moiety is attached. In some other embodiments, the coupling group CG may interrupt the backbone of the linker L. In some embodiments, the coupling group CG is triazolylene, which is the result of a reaction between an alkyne group and an azide group, either of which may be the reactive moiety or the reactive pairing moiety, as is known in the art for use in Click coupling reactions. A triazolylene group may also be further substituted. For example, a dibenzocylcooctenyl fused triazolylene moiety may result from the reaction of a conditioning modification reagent having a dibenzocyclooctynyl reactive pairing moiety $R_{px}$ with an azido reactive moiety Rx of the surface modifying ligand, which are described in more detail in the following paragraphs. A variety of dibenzocyclooctynyl modified molecules are known in the art or may be synthesized to incorporate a moiety configured to support cell growth, viability, portability, or any combination thereof.

Conditioned Surface Containing Other Components.

The conditioned surface may additionally include other components, other than or in addition to a polymer or a conditioned surface formed by a covalently linked moiety, including biologically compatible metal ions (e.g., calcium, sodium, potassium, or magnesium), antioxidants, surfactants, and/or essential nutrients. A non-limiting exemplary list includes vitamins such as B7, alpha-tocopherol, alpha-tocopherol acetate, vitamin A and its acetate; proteins such as BSA, Catalase, Insulin, Transferrin, Superoxide Dismutase; small molecules such as corticosterone, D-galactaose, ethanolamine hydrochloride, reduced glutathione, L-carnitine hydrochloride, linoleic acid, linolenic acid, progesterone, putrescine dihydrochloride, and triiodo-thyronine; and salts, including but not limited to sodium selenite, sodium phosphate, potassium phosphate, calcium phosphate, and/or magnesium phosphate. Antioxidants may include but are not limited to carotenoids, cinnamic acids and derivatives, ferulic acid, polyphenols such as flavonoids, quinones and derivatives (including mitoquinone-Q), N-acetyl cysteine, and antioxidant vitamins such as ascorbic acid, vitamin E and the like. The conditioned surface may include a culture medium supplement such as B-27® Supplement, which contains antioxidants and many of the other components listed above. B-27® Supplement is commercially available (50×), serum free from ThermoFisher Scientific, (Cat #17504044).

In some embodiments, the at least one conditioned surface may include one or more components of mammalian serum. In some embodiments, the mammalian serum is Fetal Bovine Serum (FBS), or Fetal Calf Serum (FCS). The conditioned surface may include specific components of mammalian serum such as specific amounts and types of proteins usually found in serum, which may be provided in defined amounts and type from serum free or defined media.

In other embodiments, the at least one conditioned surface does not include a mammalian serum. In various embodiments, the at least one conditioned surface may not include any titanium, nickel, or iron metal ions. In yet other embodiments, the at least one conditioned surface may not include any significant concentration of titanium, nickel, or iron metal ions. In yet another embodiment, the at least one conditioned surface may not include any gold, aluminum, or tungsten metal ions.

Any of the components of the conditioned surface, including polymers that may be flowed in to condition the surface, may be used in any combination as a surface replenishment reagent.

Fluidic Medium.

With regard to the foregoing discussion about microfluidic devices having a channel and one or more incubation chambers, a fluidic medium (e.g., a first medium and/or a second medium) can be any fluid that is capable of maintaining a reporter cell and/or biological cell of interest and, optionally a micro-object in a substantially viable state. The viable state will depend on the reporter cell, the biological cell of interest, and, if present, a micro-object, and the nature of the assay(s) being performed. For example, if the biological cell that is being evaluated by the methods described herein include analyzing for the secretion of a protein of interest, the cell would be substantially analyzable provided that it is viable and capable of expressing and secreting proteins.

The fluidic medium may provide both fluidic and dissolved gaseous components necessary for cell viability, and may also maintain pH in a desired range, using either buffered fluidic media or pH monitoring or both.

If the cell is a mammalian cell, the fluidic medium may include mammalian serum or a defined serum free medium as is known in the art, which is capable of providing essential nutrients, hormones, growth factors or cell growth signals. Similarly to the conditioned surface above, the fluidic medium may include Fetal Bovine Serum (FBS), or Fetal Calf Serum (FCS). Alternatively, the fluidic medium may not include any animal sourced serum but may be a defined medium which may include any or all of physiologically relevant metal ions (including but not limited to sodium, potassium, calcium, magnesium, and/or zinc) antioxidants, surfactants, and/or essential nutrients. A non-limiting exemplary list includes vitamins such as B7, alpha-tocopherol, alpha-tocopherol acetate, vitamin A and its acetate; proteins such as BSA, Catalase, Insulin, Transferrin, Superoxide Dismutase; small molecules such as corticosterone, D-galactaose, ethanolamine hydrochloride, reduced glutathione, L-carnitine hydrochloride, linoleic acid, linolenic acid, progesterone, putrescine dihydrochloride, and triiodo-thyronine; and salts, including but not limited to sodium selenite, sodium phosphate, potassium phosphate, calcium phosphate, and/or magnesium phosphate. Other components may be present in the fluidic medium, as is known in the art, and may be selected for a particular purpose.

In some embodiments, a suitable culture medium may include or may be composed entirely of any of Dulbecco's Modified Eagle's medium (ThermoFisher Scientific, Cat #11960-051); FreeStyle™ Medium (Invitrogen, ThermoFisher Scientific, Cat. No. 11960-051); RPMI-1640 (GIBCO®, ThermoFisher Scientific, Cat. No. 11875-127); Hybridoma-SFM (ThermoFisher Scientific, Cat. No. 12045-076); Medium E (Stem Cell, Cat. No. 3805); 1×CD CHO Medium (ThermoFisher Scientific, Cat. No. 10743-011); Iscove's Modified Dulbecco's Medium (ThermoFisher Scientific, Cat. No. 12440-061); or CD DG44 medium (ThermoFisher Scientific, Cat. No. 10743-011).

The culture medium may additionally include may include Fetal Bovine Serum (FBS, available from GIBCO®, ThermoFisher Scientific), Heat Deactivated Fetal Bovine Serum; or Fetal Calf Serum (FCS, Sigma-Aldrich Cat Nos. F2442, F6176, F4135 and others). FBS may be present at a concentration of about 1% to about 20% v/v; about 1% to about 15% v/v, about 1% to about 10% v/v, or about 1% to about 5% v/v, or any number within any of the ranges. The culture medium may additionally include Human AB serum (Sigma-Aldrich, Cat. No. S2146), and may be present in a concentration of about 1% to about 20% v/v; about 1% to about 15% v/v, about 1% to about 10% v/v, or about 1% to about 5% v/v, or any number within any of the ranges.

The culture medium may additionally include penicillin-streptomycin (ThermoFisher Scientific, Cat. No. 15140-163). The pen-strep may be present in a concentration in a range of about 0.01% to about 10% v/v; about 0.1% to about 10% v/v; about 0.01% to about 5% v/v; about 0.1% to about 5% v/v; about 0.1% to about 3% v/v; about 0.1% to about 2% v/v; about 0.1% to about 1% v/v; or any value within any of the ranges. In other embodiments, the culture medium may include geneticin (ThermoFisher Scientific, Cat. No. 101310-035). Geneticin may be present in a concentration of about 0.5 micrograms/ml; about 1.0 micrograms/ml; about 5.0 micrograms/ml; about 10.0 micrograms/ml; about 15 micrograms/ml; about 20 micrograms/ml; about 30 micrograms/ml; about 50 micrograms/ml; about 70 micrograms/ml; about 100 micrograms/ml; or any values in these ranges.

The culture medium may include a buffer. The buffer may be one of Good's buffers. The buffer may be, but is not limited to 4-(2-hydroxyethyl)-1-piperazineethanesulfonic acid (HEPES)(ThermoFisher Scientific, Cat. No. 15630-080. The buffer may be present in a concentration of about 1 millimolar; about 3 millimolar; about 5 millimolar; about 7 millimolar; about 9 millimolar; about 10 millimolar; about 12 millimolar; about 15 millimolar; about 20 millimolar; about 40 millimolar; about 60 millimolar; about 100 millimolar; or any values in these ranges.

The culture medium may additionally include a dipeptide substitute for glutamine, GlutaMAX™ (GIBCO® ThermoFisher Scientfic, Cat No. 35050-079). The substitute for glutamine may be present in a concentration of about 0.2 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges. The culture medium may include MEM non-essential Amino Acid (ThermoFisher Scientific, Cat. No. 10370-088). The MEM non-essential Amino Acid may be present in a concentration of about 0.2 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges.

The culture medium may additionally contain glucose (ThermoFisher Scientific, Cat. No. 15023-021). Glucose may be present in a concentration of about 0.1 g/L; about 0.1 g/L; about 0.1 g/L; about 0.3 g/L; about 0.5 g/L; about 0.8 g/L; about 1.0 g/L; about 1.5 g/L; about 2.0 g/L; about 2.5 g/L; about 3.0 g/L; about 3.5 g/L; about 4.0 g/L; about 5.0 g/L; about 7.0 g/L; about 10.0 g/L; or any values in these ranges.

The culture medium may additionally include mercaptoethanol (ThermoFisher Scientific, Cat. No. 31350-010). Mercaptoethanol may be present in a concentration of about about 0.001% to about 1.5% v/v; about 0.005% to about 1.0% v/v; about 0.01% to about 1.0% v/v; about 0.15% to about 1.0% v/v; about 0.2% to about 1% v/v; or any value in these ranges.

The culture medium may include OPI culture medium additive, including oxaloacetate, pyruvate, and insulin (Sigma-Aldrich, Cat. No. 0-5003). OPI culture medium additive may be present in a concentration of about 0.001% to about 1.5% v/v; about 0.005% to about 1.0% v/v; about 0.01% to about 1.0% v/v; about 0.15% to about 1.0% v/v; about 0.2% to about 1% v/v; or any value in these ranges. The culture medium may contain B-27 supplement (50×), serum free (ThermoFisher Scientific, Cat. No. 17504-163). B-27 supplement may be present in a concentration of about 0.01% to about 10.5% v/v; about 0.05% to about 5.0% v/v; about 0.1% to about 5.0% v/v; about 0.5% to about 5% v/v; or any value in these ranges.

As described herein, a culture medium or an additive for a culture medium may include one or more Pluronic® polymers useful for yielding a conditioned surface, and may include Pluronic® L44, L64, P85, F68 and F127 (including F127NF). The Pluronic® polymer may be present in the culture medium at a concentration of about 0.001% v/v to about 10% v/v; about 0.01% v/v to about 5% v/v; about 0.01% v/v to about 1% v/v, or about 0.05% to about 1% v/v. For a culture medium additive which may be provided as a kit, the concentration may be 1×, 5×, 10×, 100×, or about 100× the final culture medium concentration.

The culture medium may include IL 6 (Sigma-Aldrich, Cat. No. SRP3096-20UG). IL 6 may be present in a concentration of about 1 nM; about 5 nM, about 10 nM, about 15 nM, about 20 nM, about 25 nM, about 30 nM, about 40 nM, about 50 nM or any values in these ranges.

The culture medium may additionally include sodium pyruvate (ThermoFisher Scientific, Cat. No. 11360-070). The substitute for glutamine may be present in a concentration of about 0.1 millimolar; about 0.02 millimolar; about 0.04 millimolar; about 0.06 millimolar; about 0.08 millimolar; about 0.1 millimolar; about 0.5 millimolar; about 0.7 millimolar; about 1.0 millimolar; about 1.2 millimolar; about 1.5 millimolar; about 1.7 millimolar; about 2.0 millimolar; about 2.5 millimolar; about 3.0 millimolar; about 4.0 millimolar; about 7.0 millimolar, or about 10.0 millimolar, or any value in these ranges.

The fluidic medium may be sterile filtered through a 0.22 micron filter unit (VWR, Cat. No. 73520-986).

Summary of the System.

A system is provided for assaying at least one biological cell of interest in a microfluidic device, including a microfluidic device including a flow region configured to contain a flow of a first fluidic medium and at least one incubation chamber, wherein the at least one incubation chamber is configured to contain at least one reporter cell and the at least one biological cell of interest; and at least one reporter cell. In some embodiments, the incubation chamber may be configured to contain no more than a single biological cell of interest. In other embodiments, the incubation chamber may contain a plurality of biological cells. The incubation chamber may contain one, about 3, about 5, about 7, or fewer than 10 biological cells of interest. Fewer than ten biological cells may be 2, 3, 4, 5, 6, 7, 8, 9 or 10 cells. The biological cells may be members of a clonal population. The biological cells may be derived from a nonclonal cell population. The incubation chamber may include an isolation region. The conditioned surface of the microfluidic device may include a polymer. In various embodiments of the system, the at least one incubation chamber of the microfluidic device may have at least one surface conditioned to support cell growth, viability, portability, or any combination thereof. In some embodiments, the at least one conditioned surface of the incubation chamber may include a polymer. In some embodiments, the polymer of the at least one conditioned surface of the microfluidic device may include alkylene oxide moieties, amino acid moieties or saccharide moieties. In various embodiments, the at least one conditioned surface of the microfluidic device may include a covalently linked conditioned surface. In various embodiments, the covalently linked conditioned surface may include alkylene ether moieties, alkyl moieties, fluoroalkyl moieties, amino acid moieties, or saccharide moieties. In some embodiments, the covalently linked conditioned surface may be linked to the surface via a siloxy linking group. In various embodiments, the conditioned surface may be a monolayer. The microfluidic device of the system may include a plurality of incubation chambers.

The incubation chamber may be configured to isolate the at least one reporter cell and the at least one biological cell of interest. The incubation chamber may be configured to locate the at least one reporter cell and the at least one biological cell of interest at spatially distinct locations within the incubation chamber. In some embodiments, the reporter cell may be located at the distal end of the isolation region and the biological cell may be in the midsection or the proximal end of the isolation region. Other combinations of reporter cell placement and biological cell placement are also suitable.

The microfluidic device further may further include a flow channel that includes at least a portion of the flow region, and the incubation chamber may include a connection region that opens directly into the flow channel. The isolation region of the incubation chamber may be fluidically connected to the flow channel via the connection region and may be configured to contain a second fluidic medium, where when the flow region and the incubation chamber are substantially filled with the first and second fluidic media respectively, then components of the second fluidic medium may diffuse into the first fluidic medium and/or components of the first fluidic medium may diffuse into the second fluidic medium; and the first medium may not substantially flow into the isolation region. In some embodiments, the biological cell(s) are disposed within the isolation region and the reporter cell is located in the channel, adjacent to the proximal opening of the isolation chamber.

The reporter cell(s) may be configured to provide a detectable signal. The detectable signal may be produced when the biological cell(s) of interest include a biological activity of interest. The reporter cell(s) may be configured to produce a different detectable signal when the biological cell(s) of interest do not have the biological activity of interest. The detectable signal of the reporter cell(s) may be colorimetric, fluorescent, or bioluminescent.

The flow region (which may be a flow channel) of the microfluidic device may further include one or more capture micro-objects. Each of the capture micro-objects may include a binding substance configured to specifically bind to a biological product of the at least one biological cell of interest. The biological product may be a secreted biological product. In some embodiments, when the biological product is bound to the binding substance of the capture micro-object producing a binding product, each capture micro-object may be a bound capture micro-object. The bound capture micro-objects may be configured to be detectable. The bound capture micro-objects may be indirectly or directly detectable. The detectable signal of bound capture micro-objects may be fluorescent or chemiluminescent. The capture micro-objects may include a bead. In some embodiments, the one or more capture micro-objects may include a magnetic bead.

The capture micro-objects are in fluid connection with the one or more biological cells of interest. The one or more capture micro-objects may be located in the connection region of the incubation chamber or in the flow region proximal to the incubation chamber. In some embodiments, the capture micro-objects may be in the isolation region but may not be in physical contact with the biological cell(s). In other embodiments, the one or more capture micro-objects may not be located in the isolation region of the incubation chamber.

The detectable signal of the reporter cell(s) and the detectable signal of the bound capture micro-object(s) are may be spectrally distinct.

The microfluidic device of the system may further include at least one inlet port configured to input the first or second fluidic medium into the flow region and at least one outlet port configured to receive the first medium as it exits from the flow region. The system may be configured to perfuse the first medium within the microfluidic device to maintain cell viability. Perfusion may be irregular or periodic.

In some embodiments, the microfluidic device of the system may further include a substrate having a plurality of electrodes, wherein a surface of the substrate may form a surface of the incubation chamber and the flow region. The plurality of electrodes may be configured to generate a dielectrophoresis (DEP) force. The system may further include a selector control module configured to activate and deactivate each of the electrodes, wherein activation of an electrode may generate a dielectrophoresis (DEP) force sufficiently strong to move the biological cell(s) into or out of the at least one incubation chamber or the isolation region thereof. Each of the plurality of electrodes may be optically actuated. The DEP force may be produced by optoelectronic tweezers (OET).

In other embodiments, the microfluidic device of the system may further include a substrate having an electrode connected to a plurality of transistors, wherein a surface of the substrate may form a surface of the incubation chamber and the flow region. Each transistor of the plurality may be configured to generate a dielectrophoresis (DEP) force. The system may further include a selector control module configured to activate and deactivate each of the plurality of transistors, thereby generating a dielectrophoresis (DEP) force sufficiently strong to move the biological cell(s) into or out of the incubation chamber or the isolation region thereof. Each of the transistors may be optically actuated. In some embodiments, the DEP force may be produced by optoelectronic tweezers (OET).

In other embodiments, the microfluidic device of the system may further include a substrate having an electrode and a layer of amorphous silicon, wherein a surface of the substrate may form a surface of the incubation chamber and the flow region. The system may further include a selector control module configured to activate and deactivate the virtual electrode in the layer of amorphous silicon, thereby generating a dielectrophoresis (DEP) force sufficiently strong to move the biological cell(s) into or out of the at least one incubation chamber or the isolation region thereof. The layer of amorphous silicon may be optically activated. The DEP force may be produced by optoelectronic tweezers (OET).

Alternatively, the biological cell(s) may be moved into or out of the incubation chamber by fluid flow and/or gravity. In some embodiments, no more than one biological cell may be introduced into any incubation chamber. In some embodiments, a plurality of biological cells may be introduced into an incubation chamber. When the microfluidic device includes a plurality of isolation chambers, a plurality of biological cells may be introduced to one or more of the plurality of isolation chambers. In other embodiments, a plurality of biological cells may be introduced to each isolation chamber of the plurality. In other embodiments, fewer than ten biological cells may be introduced an incubation chamber. When the microfluidic device includes a plurality of isolation chambers, fewer than ten biological cells may be introduced to any of the plurality, or fewer than ten biological cells may be added to each isolation chamber of the plurality.

The system may be configured to move the reporter cell into or out of the incubation chamber or the isolation region thereof by fluid flow and/or gravity.

In various embodiments of the system, the biological cell may be a mammalian cell. The biological cell may be a hybridoma. The biological cell may be a lymphocyte or a leukocyte. The biological cell may be a B cell, T cell, NK cell, dendritic cell, or macrophage. The biological cell may be an adherent cell.

The system may further include a light source configured to provide excitation energy to a moiety configured to be detectable by fluorescence. The system may further include a detector configured to capture an image of the at least one incubation chamber and any biological cells contained therein. The detector may capture images under visible, infrared, or ultraviolet wavelengths of light.

Cells.

In the methods described herein, cells from many different sources may be used. The biological cell may be a mammalian cell. In some embodiments, the mammalian cell may be human, murine, porcine, or any other mammal of interest. Alternatively, the cell may be non-mammalian, e.g., a bacterial cell, a fungal cell or any kind of suitable cell. The cell may be derived from a cell culture sample or other bioproduction process. The cell may be derived from bone marrow, blood, muscle, skin, or fat. The cell may be derived from a solid tissue, bone, blood, urine, fecal, tears, sweat, synovial fluid, pleural fluid, or aqueous humor sample. The biological cell may be derived from a fine needle aspirate, lung lavage sample, or a biopsy sample.

The cell may be derived from breast and/or mammary gland, lymph node, intestinal tissue, liver, lung, neural, bone, blood, pancreatic sample, or a genitourinary tissue. The cell may be a lymphocyte or a leukocyte. The cell may be an immune cell. The cell may be a B or T cell. The cell may be an adherent cell.

The cell may be a proliferative cell. A proliferative cell may have uncontrolled growth and demonstrate disregulated growth, e.g., as in a tumor cell. A proliferative cell may alternatively have comparatively slow growth, but have high potential for differentiation such as a cancer stem cell. In some embodiments, the cell may be a tumor cell. In some embodiments, the cell may be a stem cell. In some other embodiments, the cell may be a cancer stem cell.

Any of the above listed cell types may be used in any of the methods described herein. Further, the methods are not limited to reporter cell assays of the classes of cells described specifically but may be performed with any type of cell which may be found to be of interest and may be imported into the microfluidic device described herein.

Methods of Performing Reporter Cell Assays.

Reporter cell assays of various types are commercially available, including systems providing colorimetric, fluorescent, or bioluminescent signals when the reporter cell is contacted by an expression inducing species secreted or excreted by the biological cell of interest.

Using the microfluidic devices, systems and methods described herein to perform reporter cell assays provides the ability to probe the biological activity of biological cell(s) of interest. In some embodiments, each biological cell may be placed in a separate incubation chamber in order to probe its activity without also probing activity of any other biological cell. The ability to place reporter cell(s) and biological cell(s) selectively into an incubation chamber of the microfluidic device may afford the ability to study an individual biological cell or a small group of biological cells (e.g., fewer than ten cells) without interfering signals from other cells or assay components. In other embodiments, a plurality of biological cells may be placed in the incubation chamber, and the activity of the plurality of cells may be examined without interfering signals from other cells or assay components. In some embodiments, a dielectrophoresis (DEP) force may be used to provide the selective placement of reporter cell(s), biological cell(s), and/or micro-object(s) (see below). The DEP force may be optically actuated. The dielectrophoresis (DEP) force may be provided by optoelectronic tweezers (OET).

In particular, reporter cell(s) may be introduced to a specific location in an isolation region of the incubation chamber. Reporter cells may be introduced to the distal end of an isolation region, a particular portion of an isolation region or any spatially distinct location in the isolation region such that the reporter cell(s) may not come into physical contact with the biological cell of interest.

The biological cell(s) of interest may be introduced to a specific location in an isolation region of the incubation chamber. The biological(s) cell may be introduced to a midpoint of an isolation region, while the reporter cell(s) may be at the distal end of the isolation region. In other embodiments, the biological cell(s) may be introduced to a specific location in the isolation region that is spatially distinct from the location of the reporter cell(s). Typically, the biological cell may be introduced into the isolation region such that the biological cell(s) may not come into physical contact with the reporter cell(s).

Any useful reporter cell format and signaling species may be used, where the reporter cell is configured to produce a detectable signal when the at least one biological cell produces a biological activity of interest. The detectable signal may be directly or indirectly observable. The detectable signal may be a colorimetric, fluorescent or bioluminescent signal. The fluorescent or bioluminescent signal may be produced by Förster Resonance Energy Transfer (FRET) or by Bioluminescence Resonance Energy Transfer (BRET), amongst other mechanisms. A variety of biological activities of the biological cell(s) may be probed using reporter cell assays of these classes.

Some classes of reporter cell assays include reporter genes based on beta-lactamase, beta-galactosidase, green fluorescent protein, and/or luciferase, amongst others. In some of the reporter cell assays, differentiable signals may be produced when the biological cell has/does not have the biological activity of interest, e.g., a secreted product of interest. In some embodiments of these assays, a detectable signal having a first wavelength may be produced when the biological product of interest is produced, while a detectable signal having a second wavelength is produced with none of the biological product is produced. The first and second signals may be spectrally distinct.

Additionally, the reporter cell assay may be performed simultaneously or sequentially with binding assays, where a biological product of the biological cell(s) (which may be the same or different from the biological product probed by the reporter cell assay) binds to a capture micro-object. The ability to perform more than one type of assay at the same time upon a single biological cell may be useful for multiplexing assays with limited materials and/or time. The capture micro-object may be a bead. In some embodiments, the capture-micro-object may be a magnetic bead. A capture micro-object may include a binding substance configured to specifically bind the biological product of the biological cell, forming a bound capture micro-object which may be detectable. The binding substance may be covalently or noncovalently attached to each of the micro-object(s). One non-limiting example of a binding substance may be an antibody, which may recognize the biological product. Many other classes of substances may be used as a binding substance of the capture micro-object, as is known in the art.

The bound capture micro-object(s) may be configured to be directly or indirectly detectable. A detectable signal of the bound capture micro-object(s) may be a colorimetric, fluorescent, or chemiluminescent signal. In some embodiments, the detectable signal may be produced by FRET or a separate biological species such as a pyrophosphatase, which may produce a luminescent signal.

The capture micro-object(s) may be introduced into various locations near but not in physical contact with the biological cell(s). The capture micro-object(s) may be introduced to be adjacent to a proximal opening of the incubation chamber in the flow region. In other embodiments, the capture micro-object(s) may be introduced into the connection region of the incubation region. In yet other embodiments, introducing the capture micro-object(s) may not include introducing the at least one capture micro-object to the isolation region of the incubation chamber.

SUMMARY OF SOME OF THE EMBODIMENTS OF THE METHOD

A method is provided for assaying at least one biological cell for a biological activity in a system comprising a microfluidic device having at least one incubation chamber and a flow region, the method including the steps of introducing the biological cell(s) into the incubation chamber; introducing one or more reporter cells into the incubation chamber; and analyzing the one or more reporter cells for an activity stimulated by the presence of a biological activity of the biological cell.

In various embodiments, the reporter cell(s) may be configured to produce a detectable signal when the biological cell comprises the biological activity. The detectable signal of the reporter cell(s) may be a colorometric, fluorescent, or bioluminescent signal.

The step of introducing the one or more reporter cells into the incubation chamber may be performed before the step of introducing the biological cell(s) therein. The one or more reporter cells may be introduced into an isolation region of the incubation chamber. The biological(s) cell may be introduced into an isolation region of the incubation chamber. In some embodiments, a single biological cell may be introduced into the isolation region of the incubation chamber. In other embodiments, a plurality of biological cells may be introduced into the isolation region of the incubation chamber. The biological cell(s) may be introduced to a spatially distinct region of the isolation region from the one or more reporter cells.

The step of incubating may further include providing the one or more reporter cell(s) with one or more reagents forming one or all of the components of the detectable signal of the one or more reporter cell(s).

The step of analyzing may include incubating the at least one biological cell(s) and the reporter cell(s) in the incubation chamber for a pre-determined period of time, thereby producing the detectable signal of the reporter cell(s). In some embodiments, the step of analyzing may further include analyzing the reporter cell(s) at more than one time point during the incubation period. The step of analyzing the reporter cell(s) may further include providing excitation light to excite a fluorophore of the detectable signal of the reporter cell(s).

The method(s) may further include detecting the detectable signal of the reporter cell(s). The methods may further include quantifying the detectable signal of the reporter cell(s), thereby quantifying the presence of the biological activity. In various embodiments, the one or more reporter cells may be configured to produce a second detectable signal when the at least one biological cell does not comprise the biological activity. In some embodiments, the second detectable signal may be different from the first detectable signal. For example, the first signal may have a longer wavelength from that of the second signal such that the first signal is spectrally distinct from the second signal. In various embodiments, incubating the biological cell(s) and the reporter cell(s) for the pre-determined period of time may include producing the second detectable signal of the reporter cell(s), thereby indicating an absence of the biological activity. In some embodiments, analyzing the one or more reporter cells may further include providing excitation light to excite a fluorophore of the second detectable signal of the reporter cell(s). The method may further include detecting the second detectable signal of the reporter cell(s). The method may further include quantifying the detectable signal of the reporter cell(s), thereby quantifying the absence of the biological activity.

The method(s) may further include introducing at least one capture micro-object into at least the flow region. The capture micro-object(s) may be introduced magnetically. In various embodiments, the method further includes introducing the micro-object(s) to be adjacent to a proximal opening of the incubation chamber in the flow region. In other embodiments, the micro-object(s) may be introduced into the connection region of the incubation region. In yet other embodiments, introducing the capture micro-object(s) may not include introducing the at least one capture micro-object to the isolation region of the incubation chamber. The capture micro-object(s) may include a bead. In some embodiments, the bead may be a magnetic bead.

In various embodiments of the method(s), each of the capture micro-object(s) may include a binding substance configured to specifically bind a biological product of the at least one biological cells, thereby forming a bound capture micro-object configured to be detectable. The binding substance may be covalently or noncovalently attached to each of the micro-object(s). The bound capture micro-object(s) may be configured to be directly or indirectly detectable. A detectable signal of the bound capture micro-object(s) may be a colorimetric, fluorescent, bioluminescent or chemiluminescent signal. The biological product of the biological cell may be a secreted biological product.

The method(s) may further include incubating the capture micro-object(s) during the incubation period, thereby producing the bound capture micro-object(s). The method may further include introducing one or more visualization reagents which are configured to bind to the bound capture micro-object(s) to produce the detectable signal. The visualization reagent(s) may be present during the incubation period or may be introduced after completion of the incubation period. The method may further include providing excitation light to excite the detectable signal of the bound capture micro-object(s). The method may further include detecting the detectable signal of the bound capture micro-object(s). The method may further include quantifying the detected signal of the binding substance. The detectable signal of the binding substance may be same or different from the detectable signal from the reporter cell(s). If the signals are different, the signal may be spectrally distinct.

In the method(s), the microfluidic system used to perform the assays may include any of the embodiments of the system described herein, in any combination.

In various embodiments, introducing the at least one biological cell into the microfluidic device, incubation chamber, isolation region or location within the isolation region thereof, may include using a dielectrophoresis (DEP) force having sufficient strength to move the biological cell. The DEP force may be produced by optoelectronic tweezers (OET).

In various embodiments of the method(s), introducing the reporter cell(s) into the at least one incubation chamber may include using fluid flow and/or gravity.

In various embodiments of the method(s), introducing one or more capture micro-objects into the flow region may include using fluid flow and/or gravity.

The method(s) may further include introducing a first fluidic medium into a flow channel of the flow region of the microfluidic device. In various embodiments, the rate of introducing the first fluidic medium may not sweep the isolation region of the incubation chamber.

The method(s) may further comprising perfusing the first fluidic medium during the incubating step, wherein the first fluidic medium is introduced via at least one inlet port of the microfluidic device and wherein the first fluidic medium, optionally comprising components from the second fluidic medium is exported via at least one outlet of the microfluidic device. In some embodiments, perfusing may be non-continuous. In other embodiments, perfusing may be periodic. In some embodiments, the first fluidic medium may be perfused at a rate sufficient to permit components of the second fluidic medium in the isolation region to diffuse into the first fluidic medium in the flow region and/or components of the first fluidic medium to diffuse into the second fluidic medium in the isolation region; and at the rate wherein the first medium does not substantially flow into the isolation region.

In the methods, the biological cell may be a mammalian cell. In other embodiments, the biological cell may be a hybridoma. The biological cell may be a lymphocyte or a leukocyte. The biological cell may be a B cell, NK cell, T cell, dendritic cell, or macrophage. In some embodiments, the biological cell may be an adherent cell.

A composition is provided including a biological cell and one or more reporter cells in an isolation region of a microfluidic device, where the one or more reporter cells are configured to detect a biological activity of the biological cell when contacted by a first extracellular species produced by the single biological cell. The microfluidic device of the composition may have at least one incubation chamber and a flow region, where the at least one incubation chamber includes an isolation region and a connection region, wherein the isolation region is fluidically connected to the connection region and the connection region comprises an opening directly into the flow region. The microfluidic device may include at least one conditioned surface configured to support cell growth, viability, portability or any combination thereof. The at least one conditioned surface may be covalently linked to at least one surface of the at least one incubation chamber. The at least one conditioned surface may include an alkylene ether moiety configured to support cell growth, viability, portability or any combination thereof. In other embodiments, the at least one conditioned surface may include an alkyl or fluoroalkyl (including perfluoroalkyl) moiety configured to support cell growth, viability, portability or any combination thereof. In some other embodiments, the at least one conditioned surface may include a dextran moiety configured to support cell growth, viability, portability or any combination thereof. The at least one biological cell and one or more reporter cells may be in contact with the at least one conditioned surface.

The extracellular species produced by the biological cell may contact the reporter cell(s) without the biological cell directly contacting any of the reporter cells. When the reporter cell(s) are contacted by the extracellular species, then the reporter cell(s) may be configured to produce a first detectable signal.

In some embodiments of the composition, when the reporter cell(s) are not contacted by the extracellular species, then the reporter cell(s) may be configured to produce a second detectable signal. The first detectable signal of the one or more reporter cells may be different from the second detectable signal of the one or more reporter cells. The first and the second detectable signal of the one or more reporter cells may be a colorimetric, fluorescent, or bioluminescent signal.

The composition may further include at least one capture micro-object, wherein the capture micro-object may be configured to bind an extracellular species produced by the biological cell, without physically contacting the biological cell. The extracellular species produced by the biological cell that binds to the at least one capture micro-object may be different from the extracellular species produced by the single biological cell that is detected by the one or more reporter cells. The at least one capture micro-object may not be located within the isolation region. The capture micro-object(s) may be located within the connection region. In other embodiments, the capture micro-object(s) may be located at the proximal opening of the connection region of the incubation chamber into the flow channel. In other embodiments the capture micro-object(s) may be located within the isolation region of the incubation chamber, but may not physically contact the biological cell. The capture micro-object(s) may be configured to form at least one detectable bound capture micro-object when the extracellular species binds to the capture micro-object(s). The bound capture micro-object(s) may be directly or indirectly detectable. The detectable signal of the bound capture micro-object(s) may be fluorescent or chemiluminescent.

In the composition, the biological cell may be a mammalian cell. In other embodiments, the biological cell may be a hybridoma. The biological cell may be a lymphocyte or a leukocyte. The biological cell may be a B cell, T cell, NK cell, dendritic cell, or macrophage. In some embodiments, the biological cell may be an adherent cell.

Kits. A kit is provided for assaying at least one biological cell, where the kit includes a microfluidic device having at least one incubation chamber and a flow region; and one or more reporter cells configured to test for a biological activity of the biological cell. In some embodiments, the kit may further include one or more reagents used to provide a detectable signal from the reporter cells configured to test for a biological activity of the biological cell.

The kit may further include one or more micro-objects configured to bind a biological product of the biological cell. The components of the kit may be provided in separate containers.

The microfluidic device of the kit may further include a flow channel including at least a portion of the flow region, and where the incubation chamber includes a connection region that opens directly into the flow channel. The incubation chamber may further include an isolation region. The isolation region may be fluidically connected to the connection region and may be configured to contain a second fluidic medium, where when the flow region and the at least one incubation chamber are substantially filled with the first and second fluidic media respectively, then components of the second fluidic medium may diffuse into the first fluidic medium and/or components of the first fluidic medium may diffuse into the second fluidic medium; and the first medium may not substantially flow into the isolation region. The microfluidic device of the kit may further include a plurality of incubation chambers.

The microfluidic device of the kit may further include at least one inlet port configured to input the first or second fluidic medium into the flow region and at least one outlet configured to receive the first medium, optionally containing components of the second fluidic medium, as it exits from the flow region.

The microfluidic device of the kit may include a substrate having a plurality of DEP electrodes, wherein a surface of the substrate may form a surface of the incubation chamber and the flow region. The plurality of DEP electrodes may be configured to generate a dielectrophoresis (DEP) force sufficiently strong to introduce the cell of interest into or to move one or more cells of interest out of the incubation chamber or the isolation region thereof. The plurality of DEP electrodes may be optically actuated. The DEP force may be produced by optoelectronic tweezers (OET).

In other embodiments, the microfluidic device of the kit may include a substrate having a DEP electrode connected to a plurality of transistors, wherein a surface of the substrate may form a surface of the incubation chamber and the flow region. The plurality of transistors may be configured to generate a dielectrophoresis (DEP) force sufficiently strong to introduce the biological cell or to move one or more cells of interest out of the incubation chamber or the isolation region thereof. Each of the plurality of transistors may be a phototransistor. Each of the plurality of transistors may be optically actuated. The DEP force may be produced by optoelectronic tweezers (OET).

In some other embodiments, the microfluidic device of the kit may include a substrate having a DEP electrode, wherein a surface of the substrate may form a surface of the incubation chamber and the flow region. The electrode may be configured to generate a dielectrophoresis (DEP) force sufficiently strong to introduce one or more biological cells into or move the one or more cells of interest out of the at least one incubation chamber or the isolation region thereof. The DEP electrode may be optically activated. The DEP force may be produced by optoelectronic tweezers.

In some embodiments of the kit, the microfluidic device may further include at least one conditioned surface configured to support cell growth, viability, portability or any combination thereof. In some embodiments of the kit, the kit may further include a reagent to replenish the conditioned surface. In some embodiments, the at least one conditioned surface of the at least one incubation chamber may include a polymer. In various embodiments, the polymer of the at least one conditioned surface of the microfluidic device may include alkylene oxide moieties, amino acid moieties or saccharide moieties. In other embodiments, the at least one conditioned surface of the microfluidic device may include a covalently linked conditioned surface. In various embodiments, the covalently linked conditioned surface may include alkylene ether moieties, alkyl moieties, fluoroalkyl moieties, amino acid moieties, or saccharide moieties. The at least one conditioned surface may include an alkylene ether moiety configured to support cell growth, viability, portability or any combination thereof. In other embodiments, the at least one conditioned surface may include an alkyl or fluoroalkyl (including perfluoroalkyl) moiety configured to support cell growth, viability, portability or any combination thereof. In some other embodiments, the at least one conditioned surface may include a dextran moiety configured to support cell growth, viability, portability or any combination thereof. In some embodiments, the covalently linked conditioned surface may be linked to the surface via a siloxy linking group.

While embodiments have been shown and described, various modifications may be made without departing from the scope of the inventive concepts disclosed herein. The invention(s), therefore, should not be limited, except as defined in the following claims.

It is claimed:

1. A method of assaying at least one biological cell for a biological activity in a microfluidic device that contains:
   a base;
   a microfluidic circuit structure disposed on an inner surface of the base; and
   a cover disposed over the microfluidic circuit structure,
   wherein said base, said microfluidic circuit structure, and said cover together define a set of fluidically connected microfluidic circuit elements, and
   wherein said circuit elements comprise:
      a flow region configured to contain a flow of a first fluidic medium; and
      at least one incubation chamber having a single lateral opening, wherein the single lateral opening opens laterally from the flow region, the at least one incubation chamber comprising:
         at least one surface conditioned to support cell growth, viability, portability or any combination thereof;
         an isolation region having a single opening, and configured to contain a second fluidic medium; and
         a connection region, wherein the connection region comprises a proximal opening into the flow region and a distal opening to the isolation region, and wherein the proximal opening between the flow region and the connection region is configured to facilitate substantially only diffusion between the first fluidic medium and the second fluidic medium in the isolation region when the first fluidic medium is flowing through the flow region;
   the method comprising:
      introducing the at least one biological cell into the at least one incubation chamber;
      introducing the at least one reporter cell into the at least one incubation chamber, wherein the at least one reporter cell is configured to produce a first detectable signal when the at least one biological cell comprises the biological activity; and
      analyzing the at least one reporter cell for an activity stimulated by the presence of a biological activity of the at least one biological cell.

2. The method of claim 1, further comprising introducing the at least one reporter cell into an isolation region of the at least one incubation chamber.

3. The method of claim 1, further comprising introducing the at least one biological cell into the isolation region of the at least one incubation chamber.

4. The method of claim 1, wherein the analyzing comprises incubating the at least one biological cell and the one at least one reporter cell in the at least one incubation chamber for a pre-determined period of time, thereby allowing the one at least one reporter cell to produce the first detectable signal.

5. The method of claim 4, wherein the incubating further comprises providing the one at least one reporter cell with one or more reagents forming one or all of the components of the detectable signal of the at least one reporter cell.

6. The method of claim 1, wherein the analyzing further comprises providing excitation light to excite a fluorophore of the first detectable signal of the at least one reporter cell.

7. The method of claim 6, further comprising detecting the excited fluorophore.

8. The method of claim 1, further comprising introducing at least one capture micro-object into at least the flow region.

9. The method of claim 8, further comprising introducing one or more visualization reagents which are configured to bind to the at least one capture micro-object to produce a second detectable signal.

10. The method of claim 9, further comprising detecting the second detectable signal.

11. The method of claim 1, wherein introducing the at least one biological cell into the at least one incubation chamber of the microfluidic device comprises using a DEP force having sufficient strength to move the biological cell.

12. The method of claim 11, further comprising optically actuating the DEP force.

13. The method of claim 1, wherein the at least one biological cell is a mammalian cell.

14. The method of claim 1, wherein the at least one biological cell is a hybridoma.

15. The method of claim 1, wherein the at least one biological cell is a lymphocyte or a leukocyte.

16. The method of claim 1, wherein the microfluidic device comprises at least one conditioned surface configured to support cell growth, viability, portability or any combination thereof.

17. The method of claim 1, wherein said microfluidic circuit structure is disposed between the solid support structure and the cover such that said flow of said first fluidic medium in said flow region occurs in the same layer of the microfluidic device as said second fluidic medium disposed in said incubation chamber.

18. The method of claim 1, wherein the cross-sectional height of the circuit elements is about 30 to about 200 microns.

19. The method of claim 1, wherein the width of the flow region at the proximal opening ranges from about 50 to about 1000 microns.

20. A method of assaying a biological cell for a biological activity, comprising:
   introducing a biological cell into an incubation chamber of a microfluidic device, wherein said microfluidic device comprises:
      a base;
      a microfluidic circuit structure disposed on an inner surface of the base; and
      a cover disposed over the microfluidic circuit structure,
      wherein said base, said microfluidic circuit structure, and said cover together define a set of fluidically connected microfluidic circuit elements, and
      wherein said circuit elements comprise a flow region and said incubation chamber, said incubation chamber having a single lateral opening, wherein the single lateral opening opens laterally from said flow region and further comprising:
         a surface conditioned to support cell growth, viability, portability, or any combination thereof;
         an isolation region having a single opening, and configured to contain a second fluidic medium; and
         a connection region, wherein the connection region comprises a proximal opening into the flow region and a distal opening to the isolation region, wherein the opening between the flow region and the connection region is configured to facilitate substantially only diffusion between the first fluidic medium flowing in the flow region and the second fluidic medium in the isolation region;

introducing a reporter cell into the incubation chamber, wherein the reporter cell is configured to produce a first detectable signal when the biological cell comprises the biological activity; and analyzing the reporter cell for an activity stimulated by the presence of the biological activity of the biological cell.

21. The method of claim 20, wherein the analyzing further comprises providing excitation light to excite a fluorophore of the first detectable signal of the at least one reporter cell.

22. The method of claim 20, further comprising introducing at least one capture micro-object into at least the flow region.

23. The method of claim 20, wherein introducing the at least one biological cell into the at least one incubation chamber of the microfluidic device comprises using a DEP force having sufficient strength to move the biological cell.

* * * * *